United States Patent
Iddon et al.

(10) Patent No.: US 10,687,790 B2
(45) Date of Patent: Jun. 23, 2020

(54) SAMPLING DEVICE

(71) Applicant: NEOTHERIX LIMITED, York (GB)

(72) Inventors: Peter Iddon, York (GB); Michael Raxworthy, York (GB); Lorenzo Pio Serino, York (GB)

(73) Assignee: NEOTHERIX LIMITED, Yorkshire (GB)

( * ) Notice: Subject to any disclaimer, the term of this patent is extended or adjusted under 35 U.S.C. 154(b) by 412 days.

(21) Appl. No.: 14/349,958

(22) PCT Filed: Oct. 3, 2012

(86) PCT No.: PCT/EP2012/069551
§ 371 (c)(1),
(2) Date: Apr. 4, 2014

(87) PCT Pub. No.: WO2013/050429
PCT Pub. Date: Apr. 11, 2013

(65) Prior Publication Data
US 2014/0243708 A1 Aug. 28, 2014

(30) Foreign Application Priority Data
Nov. 7, 2011 (GB) .................................. 1117296.2

(51) Int. Cl.
*A61B 10/00* (2006.01)
*A61B 5/00* (2006.01)

(52) U.S. Cl.
CPC .......... *A61B 10/0045* (2013.01); *A61B 5/445* (2013.01); *Y10T 29/49* (2015.01); *Y10T 29/49826* (2015.01)

(58) Field of Classification Search
CPC ................ A61B 10/0045; A61B 5/445; Y10T 29/49826; Y10T 29/49
See application file for complete search history.

(56) References Cited

U.S. PATENT DOCUMENTS 6,117,949 A * 9/2000 Rathi .................... A61K 9/0024
424/425
2002/0111576 A1 8/2002 Greene et al.
2007/0184222 A1 8/2007 Delouise et al.
2007/0293830 A1 12/2007 Martin
2009/0209660 A1 * 8/2009 Friess ................... A61L 27/505
514/772.3

FOREIGN PATENT DOCUMENTS

| WO | WO 97/06837 A1 | 2/1997 |
| WO | 2007103993 A2 | 9/2007 |
| WO | 2010078353 A2 | 7/2010 |
| WO | 2011086486 A1 | 7/2011 |
| WO | 2011127188 A2 | 10/2011 |

OTHER PUBLICATIONS

International Search Report (PCT/ISA/210) dated Feb. 26, 2013, by the European Patent Office as the International Searching Authority for International Application No. PCT/EP2012/069551.
Notification of Transmittal of the International Search Report (Form PCT/ISA/220) and the Written Opinion of the International Searching Authority or the Declaration (Form PCT/ISA/237) dated Feb. 26, 2013, issued in corresponding International Application No. PCT/EP20121/069551 (9 pgs).
International Search Report (Form PCT/ISA/210) dated Feb. 15, 2013, issued in corresponding International Application No. PCT/EP20121/069551 (4 pgs).
Search Report dated Mar. 6, 2012, issued in corresponding GB Application No. GB1117296.2.
European Communication dated Feb. 21, 2018, for EP Application No. 12781285.7-1122.

* cited by examiner

*Primary Examiner* — Hasan S Ahmed
(74) *Attorney, Agent, or Firm* — Buchanan Ingersoll & Rooney PC

(57) ABSTRACT

A medical sampling device, a method of manufacturing the device, and methods of testing and diagnosis using the device; a sampling dressing comprising the device, a method of manufacturing the dressing, and a method of diagnosis using the dressing; and a therapy dressing comprising the device, a method of manufacturing the dressing, and a method of treatment using the dressing. The a sampling device comprises a biodegradable porous scaffold which in use lies in contact with tissue to be sampled and comprises a fluid, in particular a reversibly thermoswitchable gel.

8 Claims, 4 Drawing Sheets

SAMPLING DEVICE

Figure 1:
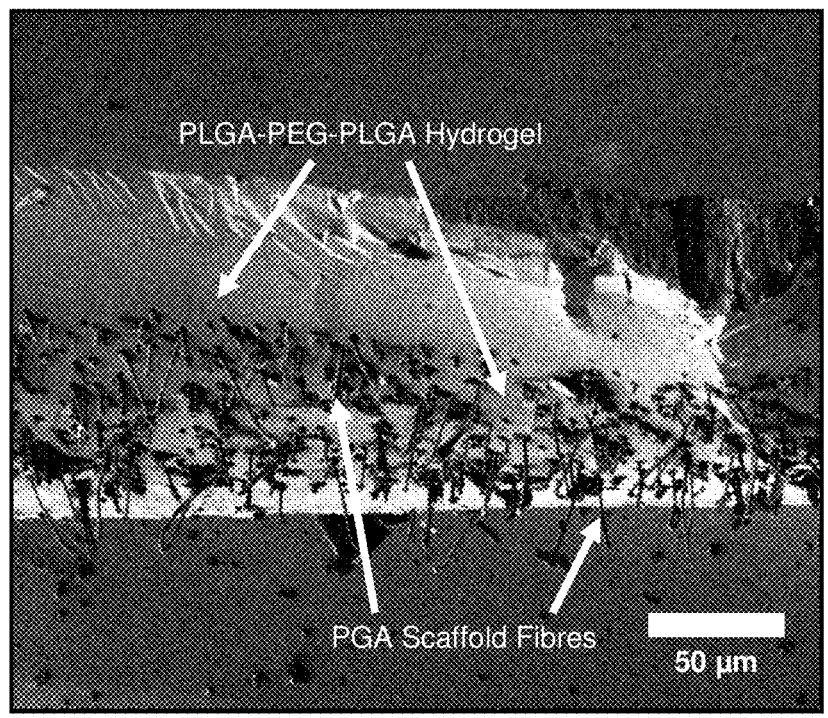

The present invention relates to a medical sampling device, a method of manufacturing the device, and methods of testing and diagnosis using the device; a sampling dressing comprising the device, a method of manufacturing the dressing, and a method of diagnosis using the dressing; and a therapy dressing comprising the device, a method of manufacturing the dressing, and a method of treatment using the dressing.

It relates in particular to such a sampling device for use in a point of care testing (POCT) device and system, and a diagnostic method that can be easily applied to a variety of wounds, to monitor the physiological status of associated soft tissue and any underlying pathologies.

It also relates in particular to such a sampling device for use in a point of use testing device and system, and a diagnostic method that can be easily applied to a variety of in vitro tissue cultures to monitor the physiological status of the soft tissue and any unwanted pathologies in the tissue.

The present invention also relates to a medical treatment device, and a method of treatment using such a device. It relates in particular to such a treatment device, and a method of treatment that can be easily applied to a variety of wounds, to help combat infections and/or any underlying pathologies.

When used herein:

The term "natural" refers to any material that is naturally occurring, for example, silk, collagen-based materials, chitosan, hyaluronic acid and alginate.

The term "synthetic" means any material that is not found in nature, even if made from naturally occurring biomaterials. Examples include, but are not limited to aliphatic polyesters, poly(amino acids), copoly(etheresters), polyalkylenes, oxalates, polyamides, tyrosine derived polycarbonates, poly(iminocarbonates), polyorthoesters, polyoxaesters, polyamidoesters, polyoxaesters containing amino groups, poly(anhydrides), polyphosphazenes and combinations thereof.

The term "biocompatible" refers to any material which when in contact with the cells, tissues or body fluids of a human or other animal does not induce adverse effects such as immunological reactions and/or rejections and the like.

The term "biodegradable" refers to any material which can be degraded, for example by proteases or by hydrolysis, in, and bioresorbed into, the physiological environment. Examples of such biodegradable materials include collagen, fibrin, hyaluronic acid, alginate and chitosan and mixtures thereof.

Examples of such biodegradable materials also include poly(L-lactic acid) (PLLA), poly(D-lactic acid) (PDLA), poly(D/L-lactic acid) (PDLLA), poly(glycolic acid) (PGA), poly(lactic acid-co-glycolic acid) (PLGA), polycaprolactone (PCL), polydioxanone (PDO), trimethylene carbonate (TMC), poly(ethylene glycol) (PEG), and mixtures thereof.

The term "scaffold" refers to any synthetic or natural porous structure used in the treatment of acute or chronic wounds, tissue engineering, regenerative medicine, or cell culture that provides a structure that supports cell attachment, migration and/or proliferation in two or three dimensions, resulting in the formation or healing of tissue. A scaffold may be biodegradable or non-degradable, and may comprise fluids, such as gases, liquids and gels, and cells in its interstices, and nutrients, and synthetic or natural biological or chemical agents, in its interstices and/or its structural members.

The term "nanofibres" in relation to a fibrous scaffold means that the majority of fibre diameters in the scaffold are less than 100 nanometres.

The term "microfibres" in relation to a fibrous scaffold means that the majority of fibre diameters in the scaffold are less than 100 micrometres.

The term "gel" in relation to the present invention refers to semi-solid colloidal systems comprising small amounts of solid material dispersed in a relatively large amount of liquid, which possess more solid-like than liquid-like characteristics. The organic or inorganic solid components of the gel can be synthetic or natural in origin. Hydrogels are defined as a gel where the liquid component is aqueous and organogels are defined as a gel where the liquid component is an organic solvent.

The term "wound" in relation to the present invention means any tissue with compromised integrity, such tissue including soft tissue, such as skin, muscle and viscera. Such wounds include acute wounds, such as gunshot, puncture, bite, surgical and infectious disease wounds; chronic wounds, such as diabetic ulcers or venous leg ulcers; and burns; and superficial, deep and cavity wounds, crush wounds, cuts, lacerations, abrasions, avulsions and velocity wounds.

The terms "marker" or "biological marker" mean biological markers or biomarkers in tissue and/or bodily fluids, which indicate the physiological status of the tissue, or tissue associated with, and in the environment of, the fluid, and any underlying pathologies. Such markers include for example, a microbial product; a part of the microbial cell contents; microbial cells which may be precursors to or propagators of wound infection, disease or other pathological condition; a substance or cell associated with a living human or animal body's response to a microbe, a wound or an endocrine or metabolic condition, such as diabetes, or with an underlying problem, for example, due to hypoxia, sepsis, biofilms or fibrosis, or risk of dehiscence or deep tissue damage.

Sampling methods are known for detecting biological markers in bodily fluids, which indicate the physiological status of tissue associated with, and in the environment of, the fluid, and any underlying pathologies. The bodily fluid may be for example wound exudate, and the tissue may be wound bed and/or tissue around the wound.

As defined hereinbefore, such markers may be, for example, a microbial product; a part of the microbial cell contents; microbial cells which may be precursors to or propagators of wound infection, disease or other pathological condition; a substance or cell associated with a living human or animal body's response to a microbe, a wound or an endocrine or metabolic condition, such as diabetes, or with an underlying problem, for example, due to hypoxia, sepsis, biofilms or fibrosis, or risk of dehiscence or deep tissue damage.

A marker may indicate in which phase in the healing process a wounds is (for example, the inflammatory or proliferative phase) and/or how far into that phase the wound is.

It may indicate a level at which infection, disease or other pathological condition might develop, and the need for diagnosis in order to combat the microbe and to create a favourable environment for tissue repair.

After antimicrobial treatment of the location the marker can give a continuing indication of whether the microbial bioburden has stayed below or again reached an unacceptable level.

Examples of a microbial product as a marker include an enzyme, in particular, an oxidase, lipase, tryptophanase, beta-lactamase, beta-lactamase inhibitor, esterase, dehydrogenase, kinase, hydrolase, protease, nuclease, phosphatase, decarboxylase, and/or carboxylase. The microbial product may also be a naturally occurring organic phosphate such as adenosine triphosphate (ATP), a pyridine nucleotide such as nicotinamide adenine dinucleotide (NADH) or a flavin such as flavin adenine dinucleotide (FADH). The microbial product may also be an exotoxin such as a superantigen, a heat-stable enterotoxin, or a pore-forming toxin.

Examples also include bacterial autoinducer signalling molecules, such as homoserine lactone derivatives, e.g. oxo-alkyl derivatives, autoinducer-2, and competence stimulating peptides.

Examples of microbial cells as markers include microorganisms of normal skin or mucosa flora such as *Staphylococcus epidermidis, Staphylococcus aureus, Corynebacterium, Brevibacterium, Proprionibacterium acnes, Pityrosporum, Candida albicans*; and microorganisms such as coagulase-negative *Streptococci, E. coli, Proteus, Klebsiella pneumoniae, anaerobes, Pseudomonas aeruginosa, Acinetobacter, Stenotrophomonas maltophilia*.

Examples of a substance associated with a living human or animal body's response to a microbe as a marker include enzymes such as lysozyme, complement and phospholipase A2, antimicrobial peptides such as cathelicidin and the β-defensins, and secretory antibodies such as immunoglobulin A.

Examples of a substance associated with a living human or animal body's response to a wound include markers of the inflammatory phase, or early stage expression markers (up to day 2), such as
PDGF, TGF-β, KRT17, K6HF, TNF-α, IGF-1, CXCR4, CD68, IL1, IL10, IFNγ, CD44 and CD11C;
markers such as those involved in oxidative stress on the wound bed, such as iron II and iron III salts;
proteases, such as serine proteases, e.g. elastase, thrombin; cysteine proteases matrix metalloproteases, e.g. collagenase; and carboxyl (acid) proteases; and endotoxins and/or inflammatories, such as lipopolysaccharides, and histamine.

Examples of a substance associated with a living human or animal body's response to a wound include proliferative phase markers or late expression markers (days 4-8), such as cell migration and proliferation factors, such as VEGF, BFGF, IL10, MMP2, CTGF, MMP-9, IL2, IL4, IL6, IL8, CD99, type V collagen, FGF, VEGFR, NRP-1, Ang1 and Ang2, PDGFR, MCP-1, $\alpha_v\beta_3$, $\alpha_v\beta_5$ and $\alpha_5\beta_1$, VE-cadherin, CD31, ephrin, plasminogen activators, eNOS, COX-2 AC133 and Id1/Id3; and extracellular matrix, including matrix macromolecules, such as collagen, hyaluronic acid, fibronectin, laminin, elastin, proteoglycans such as agrin, perlecan, versican, decorin and fibromodulin, and sulphated glycosaminoglycans (GAGs) such as heparin sulphate, chondroitin sulphate and keratin sulphate.

Examples of a substance associated with a living human or animal body's response to a wound include continuous expression markers, such as HSP70, MIF, CD6, TIMP1 and TIMP2

Examples of a substance associated with a living human or animal body's response to a wound include reduced expression markers, such as PIP5K28, endothelial-1, TYRP1 and KRT2A.

Examples of cells associated with a living human or animal body's response to a wound include proliferative phase markers, such as fibroblasts, keratinocytes, endothelial cells, inflammatory cells.

Examples of a substance associated with a living human or animal body's response to an endocrine or metabolic condition, such as type I or type diabetes, as a marker include
islet cell cytoplasmic autoantibodies, glutamic acid decarboxylase antibodies, insulinoma-associated-2 autoantibodies, C-peptide, insulin autoantibodies, or an enzyme such as β-glucuronidase, N-acetyl-β-glucosaminidase, acid phosphatase, amylase, alkaline phosphatase, trehalase, aldolase, arginase, lipase, cholinesterase.

It is known, in current methods of monitoring and diagnosis of wounds to carry out wound sampling with an absorbent dipstick or swab, a spatula or spoon, or a syringe, with or without elution of the wound, or by way of biopsies.

Such conventional wound sampling methods suffer from the disadvantage that they are invasive and usually involve contact with the wound bed, and are therefore usually painful, biopsies cause further damage to the wound and/or any scaffold in the wound, and the other sampling methods above may often do so.

Such conventional wound sampling methods also suffer from the disadvantage that they do not readily lend themselves to use with, and are consequently not often used with a point of care diagnostic testing (POCT) system, and samples usually have to be sent away to a central testing facility for analysis using a diagnostic assay device.

Only once the physiological status of the tissue associated with, and in the environment of, the wound fluid, and/or any underlying pathologies have been identified, can necessary therapy be identified and implemented cost-effectively to remove these adverse conditions. By the time an assay result has returned to the relevant medical practitioner, and the cause and appropriate therapy for any lack of healing or infection is obvious, the opportunity for early intervention may have been missed.

Conventional wound sampling devices cannot be easily applied to a variety of wounds, including acute and chronic wounds, to monitor the physiological status of associated soft tissue and any underlying pathologies. It would be desirable to provide a sampling device which avoids these disadvantages of known wound diagnostic sampling devices and can be easily applied to a wide variety of bodily locations, but in particular to wounds, to monitor the physiological status of the relevant tissue, for example by wound care physicians, plastic surgeons, dermatologists and podiatrists, running wound clinics or in private practice as part of POC diagnosis and therapy, in particular using a sampling device with a POC diagnostic marker assay device.

It is also known, in current methods of tissue engineering to grow tissue in vitro on a porous biodegradable scaffold. Such conventional tissue engineering methods suffer from the disadvantage that it is relatively difficult to assess and monitor the physiological status of the tissue growing on the scaffold or to monitor and identify the onset of any pathologies or other adverse conditions in the tissue, using biological markers.

Examples of markers associated with cell proliferation include proliferative phase markers or late expression markers, such as
cell migration and proliferation factors, such as VEGF, BFGF, IL10, MMP2, CTGF, MMP-9, IL2, IL4, IL6, IL8, CD99, type v collagen, FGF, VEGFR, NRP-1, Ang1 and Ang2, PDGFR, MCP-1, $\alpha_v\beta_3$, $\alpha_v\beta$ and $\alpha_5\beta_1$, VE-cadherin, CD31, ephrin, plasminogen activators, eNOS, COX-2 AC133 and Id1/Id3; and extracellular matrix, including matrix macromolecules, such as collagen, fibronectin, elastins, proteoglycans, such as glycosaminoglycans (GAGs) and heparin sulphate, perlecan and agrin.

Markers for potential undesirable pathologies include those microbial products, parts of microbial cell contents, and microbial cells which may be precursors to or propagators of wound infection, disease or other pathological condition, listed hereinbefore in relation to wound markers.

Such conventional wound sampling methods also suffer from the disadvantage that they do not readily lend themselves to use with a point of use testing system, so that it is difficult to carry out tissue assessment and monitoring quickly.

We have surprisingly found that all the above disadvantages may be overcome by a sampling device in which an porous scaffold is applied to a wound, or acts as a tissue engineering scaffold.

Accordingly, in a first aspect of the present invention there is provided a sampling device that comprises a biodegradable porous scaffold which in use lies in contact with tissue to be sampled, characterised in that the scaffold comprises a fluid.

In one embodiment of the first aspect of the present invention there is provided a conformable wound sampling device that comprises a biodegradable porous scaffold which in use lies in contact with the wound bed, characterised in that the scaffold comprises a fluid.

In another embodiment of the first aspect of the present invention there is provided a sampling device that comprises a biodegradable porous scaffold on which is use tissue is grown in vitro, characterised in that the scaffold comprises a fluid.

The fluid provides a medium into which desired materials, such as markers may infiltrate. Such markers may be for example, a microbial product, a part of the microbial cell contents, microbial cells; or a substance or cell associated with a living human or animal body's response to a microbe, a wound or an endocrine or metabolic condition, infiltrating from a wound bed; or markers of the stage of development of tissue growing on the scaffold, infiltrating from the tissue.

The fluid may be readily isolated, and the markers assayed, preferably in a conventional point-of-care test (POCT) or point-of-use diagnostic assay device.

In the case of the present wound sampling device, once the physiological status of the tissue associated with the wound fluid, and/or any underlying pathologies have been identified, any necessary surgical procedures can be scheduled to occur cost-effectively once these adverse conditions are removed. This translates advantageously into earlier patient discharge and thus savings to health systems.

The present wound sampling device and a method of using it have the advantage that they are no more invasive than a dressing wound contact layer or wound scaffold for tissue regrowth, and its use, and are therefore not painful, and cause no further damage to the wound. The present wound sampling device may indeed also act simultaneously as a tissue regrowth scaffold.

The wound sampling device also has the advantage that it readily lends itself to use with a point of care diagnostic testing (POCT) system, and samples thus do not have to be sent away to a central testing facility for diagnostic assay device.

Because an assay result is quickly available to the relevant medical practitioner, for example a wound care physician, plastic surgeon, dermatologist or podiatrist, running a wound clinic or in private practice, as part of POC diagnosis and therapy, the opportunity for early intervention will not be missed.

The present wound sampling device can also be easily applied to a variety of wounds, including acute and chronic wounds, to monitor the physiological status of associated soft tissue and any underlying pathologies.

In some embodiments of first aspect of the invention, the sampling device fluid is or comprises one or more liquid materials. Suitable materials include water, for example purified water, aqueous salt solutions, for example isotonic saline solution, buffer solutions, for example phosphate buffer solution, and alcohols, for example ethanol, and mixtures thereof.

In some other embodiments of first aspect of the invention, the sampling device fluid is or comprises one or more gel materials. Suitable materials include hydrogels, for example hydrogels based on poly(acrylic acid), polyacrylamide, poly(vinyl alcohol), poly(ethylene oxide), poly(2-hydroxyethyl methacrylate), poly(2-acrylamido-2-methyl-1-propanesulfonic acid), polyvinylpyrrolidone, polypeptides, silicones, polyurethanes, polyesters, polyacrylates, polymethacrylates, agarose, alginate, collagen, chitosan, hyaluronan, fibrin, proteins, and silk, and derivatives and mixtures thereof; and organogels, for example organogels based on lecithin, glyceryl fatty acid esters, sorbitan esters, polyethylene, and poly(methacrylic acid-co-methylmethacrylate), and derivatives and mixtures thereof. The gel materials can be homogenous or dispersed within a liquid medium, or may optionally be used in a dry state and converted to a gel following absorption of bodily fluid, wound exudate or cell culture medium.

In preferred embodiments of first aspect of the invention, the sampling device fluid is or comprises one or more thermo-switchable gel materials. Such materials switch from a liquid to a gel at a given temperature or over a given temperature range. Preferred materials include those that thermally gel, that is switch from a liquid below a given temperature or temperature range to a gel above that temperature or temperature range.

Preferred materials include those that switch reversibly through a given temperature or temperature range. These include polymers and copolymers based on polylactide, poly(lactide-co-glycolide), polycaprolactone, poly(propylene oxide), poly(butylene oxide), poly(vinyl methyl ether), poly(N-isopropylacrylamide), poly[2-(N-morpholino)ethyl methacrylate], and poly[2-(dimethylamino)ethyl methacrylate], and derivatives and mixtures thereof.

Preferred materials for wound sampling device fluids include those that switch, and in particular thermally gel, especially reversibly thermally gel, at or near normal body temperature for the human or animal patient. Preferred materials for tissue engineering sampling devices include those that switch, and in particular thermally gel, especially reversibly thermally gel, at or near the optimum incubation temperature for the tissue grown on the scaffold.

Other preferred materials do not reversibly thermally gel, but may be converted to a liquid form by diluting the gel below its critical gelation concentration, or by the addition of an additive that disrupts the gel structure, such as an appropriate solvent or salt.

In addition to gels that respond to changes in temperature, gels can also be formed from suitable precursor fluids by the action of stimuli such as the presence of chemical species, changes in pH, pressure, light, electric fields and magnetic fields. This type of gel formation may optionally be reversible.

Such materials are preferred because of the convenience in use which they provide, as described further below.

When in the porous scaffold of the device in use, it is preferred that the fluid is a gel or other similar material so that it can function as a medium into which the desired materials, such as markers may diffuse, or cell types may migrate and proliferate, from the wound bed or the tissue growing on the scaffold, but the fluid does not leak from the scaffold.

However, it is preferred that some, if not substantially all, of the fluid is a relatively low viscosity liquid at room temperature.

A relatively low viscosity greatly eases the loading of the fluid into the scaffold before or after placing the scaffold on the wound bed or seeding the scaffold with cells, and the liquid can conform exactly to the shape of the wound and/or scaffold, with no air gaps.

It is preferred that the fluid is reversibly switchable, by reverting to being a liquid on dilution or on being treated with a structure disruptant, or by being thermo-switchable, so that once a desired quantity of the desired markers have diffused, or where the markers are cell types that have migrated and proliferated, from the wound bed into the fluid in the scaffold, substantially all of the fluid reverts to a liquid on being diluted, disrupted or cooled to room temperature, since this greatly eases the isolation of the fluid from the scaffold, for assaying for the markers.

Being able to reverse the transition means that the sample gel containing the markers can be retrieved rapidly as a liquid from the scaffold, which may be left in situ in the wound or incubation chamber or removed from the wound or incubation chamber for handling. Where appropriate, cooling of the gel may be achieved by means of a cooled sampling probe, placing a sample of gel on a cooled surface or in a refrigerator, or by any other known method of cooling, such as simply washing the scaffold with cool liquid (for example saline at 10-15° C.) to reverse the gelation and wash out the resultant liquid. The liquid is then easily analysed in an assay, requiring little or no prior processing.

Preferred fluids of this type in wound sampling devices are bioresorbable. Advantageously, such a fluid does not have to be entirely washed out or removed from the wound, since any remaining gel does not persist in the wound. This further reduces the risk of pain and damage to the wound and/or scaffold, and saves time.

Suitable reversible thermo-switchable materials include those based on poly(hydroxyalkanoic acids), such as poly (L-lactic acid), poly(D-lactic acid), poly(D/L-lactic acid), poly(glycolic acid), poly(glycolic acid-co-lactic acid), polydioxanones, polycaprolactone, and those based on poly (alkylene oxides), such as poly(ethylene oxide) (PEO), also known as poly(ethylene glycol) (PEG), poly(propylene oxide) and poly(butylene oxide), and copolymers and mixtures thereof.

In preferred embodiments of the invention the material comprises a copolymer of a glycolide and/or a lactide and/or other suitable hydroxy acids and/or a poly(ethylene glycol) (PEG).

Examples of suitable copolymers include triblock copolymers that contain poly(lactic acid-co-glycolic acid) (PLGA) random copolymer end blocks and a poly(ethylene glycol) (PEG) homopolymer central block. Any such triblock copolymer may be represented by the following formula: PLGA-PEG-PLGA. Typical molecular weights for the PLGA end blocks are in the range 1,500-3000. The molecular weight for the central PEG block is typically 1,000 or 1,500.

The fluid may comprise an aqueous solution of the copolymer, typically at 10-50 w/v %.

It is believed that gelation of the triblock copolymer solution is a physical change brought about by changes in polymer solubility as the temperature is changed. At temperatures below the lower consolute solution temperature (LCST) of the PLGA polymer blocks, the triblock copolymer is soluble in water. As the temperature is increased above the LCST, hydrogen bonding between the water and the PLGA blocks is disrupted and the polymer becomes increasingly insoluble. If the solution concentration is high enough, a gel is formed when collapse of the PLGA blocks forms micelles comprising insoluble polymer microdomains surrounded by the still-soluble PEG polymer. The process is thermally reversible.

A wound sampling device of the first aspect of the invention may be made up and used in a number of ways, all of which comprise loading the scaffold reversibly or irreversibly with the fluid, depending on whether the fluid is switchable, whether it is reversibly switchable and whether it is switchable at or near normal body temperature for a human or animal patient, or at or near the optimum incubation temperature for tissue grown on the scaffold.

Thus, in the case of a wound sampling device
a) the scaffold may be loaded with the fluid and the resultant sampling device placed in a wound, or
b) the scaffold may be placed in a wound and then loaded with the fluid.

In option b) the liquid may be added to the scaffold immediately after the scaffold is placed in the wound, or there may if desired be a time delay between applying the scaffold and applying the fluid to the scaffold.

In either option, several fluid applications may be made to the same scaffold over the course of the wound healing, usually with removal of at least some of the fluid from the scaffold before the next application of fluid. The fluid may penetrate entirely into the scaffold, penetrate partially into the scaffold, or maintain intimate and direct contact with the outer surface of the scaffold.

In either option, the scaffold or device may be held in place in the wound by a dressing backing layer, optionally with, for example a foam wound filler for intimate contact with wound bed, and optionally removably or irremovably attached to backing layer or wound filler. Such dressings form a third aspect of the present invention, described further hereinafter.

In the case of a tissue engineering sampling device
a) the scaffold may be loaded with the fluid and the resultant sampling device, or
b) the scaffold may be seeded with the relevant tissue cells and then loaded with the fluid.

In option b) the liquid may be added to the scaffold immediately after the scaffold is seeded with cells, or there may if desired be a time delay between seeding the scaffold and applying the fluid to the scaffold.

In either option, several fluid applications may be made to the same scaffold over the course of the tissue growth, usually with removal of at least some of the fluid from the scaffold before the next application of fluid.

The fluid is often contained in at least part of the accessible and otherwise empty interstices between the fibres of the scaffold, preferably in more than 50% of the interstices, more preferably between 75 and 100%, and most preferably in substantially all of the interstices.

The fluid may be uniformly distributed in the scaffold, or the majority of the fluid may lie towards the periphery of the scaffold, with the core of the scaffold being substantially free of fluid.

In both embodiments, it is preferred that some, if not substantially all of the fluid is uniformly distributed over the periphery of the scaffold, since that part of the scaffold comprises its interface with the wound bed or growing tissue, which must be crossed by the desired markers.

The distribution of the fluid in the scaffold will often depend on the way in which the scaffold is made up and used, that is in the case of a wound sampling device on whether a) the scaffold is loaded with the fluid and the resultant sampling device placed in a wound, or
b) the scaffold is placed in a wound and then loaded with the fluid.

The distribution of the fluid will depend on how dry the scaffold is. In option a), the scaffold will be entirely dry, and an entirely dry scaffold will probably be entirely permeated by the fluid. However, in option b), whether it is an initial or repeat loading, the scaffold will usually be wet to some degree, depending on the amount and rate of wound exudate, whether the wound or the scaffold has been recently irrigated, and the length of time the scaffold is in contact with the wound bed, and the fluid will not permeate throughout the scaffold due to the presence of wound exudate and/or irrigant in the scaffold.

In the case of a fluid which thermally gels to a gel at or near normal body temperature for the human or animal patient, the permeation of the fluid will also depend on the temperature distribution within the scaffold, which in turn will depend on the length of time the scaffold is in contact with the wound bed, as the fluid in viscous gel form at or near body temperature will not penetrate as far as in its form of a relatively low viscosity liquid at room temperature. Depending on the amount and distribution of other fluids and temperature in the scaffold, the fluid will be confined to surface of the scaffold distal of the wound bed or will penetrate part way into the scaffold.

It is preferred that the scaffold is initially applied to the wound bed, and the fluid is applied afterwards.

It is also preferred that, irrespective of the distribution of fluid within the scaffold, sufficient fluid extends beyond the surface of the scaffold to facilitate sampling of the fluid, and there is no gap between the fluid in the scaffold and on the surface. Thus desired materials, such as markers will infiltrate into and diffuse through the fluid within the scaffold to the fluid on the surface of the scaffold.

Similar considerations apply to the loading of the fluid into the scaffold of a tissue engineering device before or after seeding the scaffold with the relevant cells, replacing wound exudate and irrigant with nutrient fluid, and body temperature with incubator temperature.

The fluid when applied is usually a relatively low viscosity liquid at room temperature, since this greatly eases the loading of the fluid into the scaffold before or after placing the scaffold on the wound bed or seeding the scaffold with cells, and the liquid can conform exactly to the shape of the wound and/or scaffold. Such a fluid may be applied by syringe, pipette or aerosol, or poured on from a bottle or other vessel, preferably with a spout or nozzle.

As regards suitable and preferred materials for the scaffold, a number of tissue scaffold methods exploit the biological properties of relatively pure natural polymers. Examples of these include as collagen, fibrin, silk, alginate, chitosan and hyaluronate extracted from animal or plant tissue, and mixtures thereof. Others are based upon processed extracellular matrix (decellularised) materials which contain multiple natural macromolecules. An example of such a scaffold is Oasis® (Healthpoint Limited), a biologically derived extracellular matrix-based wound product comprised of porcine-derived acellular small intestine submucosa which contains type I collagen, glycosaminoglycans and some growth factors.

However, there are concerns over the use of natural polymers because of the potential pathogen transmission, immune reactions, poor handling, mechanical properties and less controlled biodegradability. As a result, synthetic polymeric materials are preferred for use in the scaffolds of the sampling devices of the first aspect of the present invention.

The scaffold may be made of any biocompatible synthetic material (as hereinbefore defined), but such material is preferably biodegradable (as hereinbefore defined, which means that the material is bioresorbable into, the physiological environment.

Examples of such synthetic biodegradable materials include poly(L-lactic acid) (PLLA), poly(D-lactic acid) (PDLA), poly(D/L-lactic acid) (PDLLA), poly(glycolic acid) (PGA), poly(lactic acid-co-glycolic acid) (PLGA), polycaprolactone (PCL), polydioxanone (PDO), poly(trimethylene carbonate) (PTMC), poly(ethylene glycol) (PEG), and mixtures thereof.

The scaffold may be in any porous form so dimensioned that in use, the desired materials, such as markers may diffuse, or cell types may migrate and proliferate, from the wound bed or the tissue growing on the scaffold, into the fluid in the scaffold.

The scaffold may thus be a porous body, such as a foam. This may be in the form of at least one layer or sheet, optionally bonded to each other and/or to the backing layer membrane with an adhesive or thermally. The or each foam may be in a range of various forms, but should be open-cell foams.

In some embodiments of the invention, the majority of pore diameters in the foam scaffold are less than 100 microns. Suitable materials for a foam scaffold include biodegradable polymers such as PLLA, PDLA, PDLLA, PGA, PLGA, PCL, PDO, PTMC, and PEG, and derivatives and mixtures thereof; and
non-biodegradable polymers such as silicones, polyurethanes, polyesters, polyacrylates, polymethacrylates, polystyrene, and polyolefins, and derivatives and mixtures thereof; and
natural polymers such as agarose, alginate, collagen, chitosan, hyaluronan, fibrin, other proteins, and silk, and derivatives and mixtures thereof; and other materials such as ceramics, metals, and glasses.

The scaffold may additionally or (preferably) alternatively comprise a porous body such as a non-woven, woven or knitted textile fabric, again so dimensioned that in use, the desired materials, such as markers may diffuse, or cell types may migrate and proliferate, from the wound bed or the tissue growing on the scaffold, into the fluid in the scaffold.

In preferred embodiments of the invention the scaffold is a non-woven. Non-woven fabrics are those which are neither woven nor knit and which are typically manufactured by putting small fibres together to form a sheet or web, and then binding them together.

They may be bound mechanically (as in the case of felt, by interlocking them with serrated needles such that the inter-fibre friction results in a stronger fabric), with an adhesive, or thermally (by applying binder (in the form of powder, paste, or polymer melt) and melting the binder onto the web by increasing temperature).

In more preferred embodiments of the invention the scaffold is manufactured by electrospinning (either solution or melt electrospinning), phase separation, melt-blowing, spinning or self-assembly.

Electrospinning is the preferred method of manufacture because it readily allows scale-up to industrial levels of production, particularly in terms of appropriately sized scaffolds for use in medical applications.

The technique of electrospinning was first introduced in the early 1930s to fabricate industrial or household non-woven fabric products. In recent years, the technique has been utilised to form scaffolds of polymer fibres for use in tissue engineering. The technique involves forcing a natural or synthetic polymer solution through a capillary, forming a drop of the polymer solution at the tip and applying a large potential difference between the tip and a collection target.

When the electric field overcomes the surface tension of the droplet, a polymer solution jet is initiated and accelerated towards the collection target. As the jet travels through the air, the solvent evaporates and a non-woven polymer fabric is formed on the target.

Such fibrous fabrics, having an average fibre diameter in the micrometre or nanometre scale, have been used to fabricate complex three-dimensional scaffolds for use in tissue engineering applications.

We have identified scaffolds having an architecture allowing them to act as a sampling device for use in contact with a wound bed or as a sampling device which facilitates tissue proliferation. They also demonstrate dimensional stability (with low or negligible scaffold shrinkage, loss of initial fibrous architecture and reduction in initial pore size) over the time required for the sampling processes.

Examples of suitable biodegradable materials for the scaffold (as defined hereinbefore) within or as the sampling device wound contact integer include biodegradable and/or bioabsorbable materials. Examples of these include naturally occurring materials, for example keratin, laminin, elastin, collagen and extracellular matrix proteins, and synthetic materials, for example aliphatic polyesters, in particular poly(hydroxyalkanoic acids), such as poly(L-lactic acid), poly(D-lactic acid), poly(D/L-lactic acid), poly(glycolic acid), poly(glycolic acid-co-lactic acid), polydioxanones, polycaprolactone, and blends and co-polymers thereof.

In preferred embodiments of the invention the fibre comprises a copolymer of a glycolide and/or a lactide and/or other suitable hydroxy acids and/or internal esters. Examples of suitable copolymers include poly(lactic acid-co-glycolic acid) (PLGA), a copolymer with lactic acid; poly(glycolide-co-caprolactone) (PGACL), a copolymer with [epsilon]-caprolactone and poly(glycolide-co-trimethylene carbonate) (PGATMC), a co-polymer with trimethylene carbonate.

In preferred embodiments of the invention the copolymer is poly(lactic acid-co-glycolic acid) (PLGA), wherein the ratio of GA:LA is about 85:15, or about 85.25:14.75, or about 85.50:14.50, or about 85.75:14.25; or about 90:10, or about 90.25:9.75; or about 90.50:9.50; or about 90.75:9.25; or about 91:9; or about 92:8; or about 93:7; or about 94:6; or about 95:5; or about 96:4; or about 97:3; or about 98:2; or about 99:1.

In other preferred embodiments of the invention the fibre comprises polycaprolactone (PCL) and copolymers thereof with other hydroxyalkanoic acids and/or internal esters.

The invention further covers blends of PGA and a polyester. Examples of suitable blends include poly(glycolic acid) blended with poly(lactic acid) (PGA/PLA) and also polydioxanone blended with poly(glycolic acid) (PDO/PGA). It is envisaged that the blends may comprise at least one copolymer.

All stereoisomeric forms of the polymers fall within the scope of the present invention.

The above suitable and preferred materials for the scaffold may be solvent spun using appropriate solvents, such as dimethylformamide, methylene chloride, chloroform, dichloromethane, acetonitrile, methanol, N-methylpyrolidone, hexafluoroisopropanol and dimethyl sulphoxide.

Such solvents may contain appropriate additives, such as sodium chloride, sodium acetate, magnesium chloride, potassium dihydrogen phosphate, potassium iodate and potassium phosphate calcium carbonate, calcium phosphate and calcium lactate, in solution form or in nanoparticulate forms, and any other additives, solvents, polymers, bioactives, pharmaceutical agents, metals, metal oxides or cells or cellular components known to one skilled in the art, that can be integrated into an spun format.

Where the wound integer comprises a wound filler, the materials may be deposited onto and/or attached to the surface of the wound filler by any means known to those skilled in the art. They may be spun, for example electrospun, onto the wound filler.

In some embodiments of the invention the mean fibre diameter in the fibrous scaffold is between from about 50 nanometres to 50 microns, particularly of from about 0.1 to 10 microns and more particularly of from about 1.2 to 4.0 microns. In preferred embodiments of the invention the scaffold comprises electrospun fibres, typically having a mean fibre diameter of from about 1.2 to 4.0 microns, particularly of from about 1.5 to 3.5 microns and more particularly of from about 1.9 to 2.8 microns.

The fibres may be continuous, semi-continuous or staple fibres.

In some embodiments of the invention the fibrous scaffold may have a pore size of 1 to 50 microns, preferably between 3 and 35 microns, more preferably between 4 and 25 microns, and more preferably between 5 and 20 microns.

In some embodiments of the invention the fibrous scaffold comprises more than one type of fibre within the same layer, where the different fibres are characterised by having different mean fibre diameters or are made of different materials.

In some embodiments of the invention the fibrous scaffold comprises more than one layer of fibres, where the different layers are characterised by having different mean fibre diameters, different pore sizes, different porosities, or are made of different materials.

According to a preferred embodiment of the invention there is provided a sampling device with a scaffold which
a) comprises fibres of a polymer comprising glycolide residues,
b) comprises fibres having a mean fibre diameter of between from about 1.5 to 3.5 microns, and
c) contains a fluid which is a liquid which reversibly thermally gels at about body temperature.

In some forms of this embodiment of the first aspect of the invention the polymer is PGA.

In some forms of this embodiment of the invention the polymer content of the fibre comprises over 85% glycolide, over 90% glycolide, over 95% glycolide, or consists of 100% glycolide residues. The polymer may also comprise lactide residues.

Poly(glycolic acid) (PGA) also referred to as polyglycolide, and copolymers of glycolic acid (GA) with other hydroxyalkanoic acids or internal esters, such as lactic acid (LA) or caprolactone (CL), are biodegradable, thermoplastic polymers. PGA may be prepared from GA by means of polycondensation or ring-opening polymerisation of glycolide. Copolymers of GA with other hydroxyalkanoic acids or internal esters may be prepared from glycolic acid (GA) and the other acid by polycocondensation and/or ring-opening copolymerisation.

PGA and GA copolymers are characterised by hydrolytic instability owning to the presence of the ester linkage in the backbone, and thus when exposed to physiological conditions, they are degraded by random hydrolysis. The degradation products, glycolic acid and/or the hydroxyalkanoic acids or internal ester are non-toxic and can enter the tricarboxylic acid cycle after which they are excreted as water and carbon dioxide. The polymers have been shown to be completely resorbed by an organism in a time frame of four weeks to six months.

According to another preferred embodiment of the invention there is provided a sampling device with a scaffold which
a) comprises fibres of a polymer comprising caprolactone residues,
b) comprises fibres having a mean fibre diameter of between from about 1.5 to 3.5 microns, and
c) contains a fluid which is a liquid which reversibly thermally gels at about body temperature.

In some forms of this embodiment of the first aspect of the invention the polymer is PCL.

Polycaprolactone (PCL) and copolymers of caprolactone (CL) with other hydroxyalkanoic acids or internal esters are also biodegradable, thermoplastic polymers.

PCL may be prepared from CL by means of ring-opening polymerisation. Copolymers of GA with other hydroxyalkanoic acids or internal esters may be prepared from CL and the other acid by polycocondensation and/or ring-opening copolymerisation. PCL and GA copolymers are also characterised by hydrolytic instability owning to the presence of the ester linkage in the backbone, and consequently when exposed to physiological conditions, they are also degraded by random hydrolysis.

The degradation products, CL and/or the hydroxyalkanoic acids or internal ester are non-toxic and can enter the tricarboxylic acid cycle after which they are excreted as water and carbon dioxide.

A second aspect of the present invention provides a method of manufacturing a wound sampling device of the first aspect of the invention, which method comprises loading the scaffold reversibly or irreversibly with the fluid.

As noted hereinbefore, a wound sampling device of the first aspect of the invention may be made up and used in a number of ways, all of which comprise loading the scaffold reversibly or irreversibly with the fluid.

Whether the scaffold is loaded reversibly or irreversibly will depend on whether the fluid is switchable, whether it is reversibly switchable and whether it is switchable at or near normal body temperature for a human or animal patient, or at or near the optimum incubation temperature for tissue grown on the scaffold.

Thus, in the case of a wound sampling device
a) the scaffold may be loaded with the fluid and the resultant sampling device placed in a wound, or
b) the scaffold may be placed in a wound and then loaded with the fluid.

In option b) the liquid may be added to the scaffold immediately after the scaffold is placed in the wound, or there may if desired be a time delay between applying the scaffold and applying the fluid to the scaffold.

In either option, several fluid applications may be made to the same scaffold over the course of the wound healing, usually with removal of at least some of the fluid from the scaffold before the next application of fluid.

In either option, the scaffold or device may be held in place in the wound by a dressing backing layer, optionally with, for example a foam wound filler for intimate contact with wound bed, and optionally removably or irremovably attached to backing layer or wound filler. Such dressings form a third aspect of the present invention, described further hereinafter.

In the case of a tissue engineering sampling device
a) the scaffold may be loaded with the fluid and the resultant sampling device seeded with the relevant tissue cells, or
b) the scaffold may be seeded with the relevant tissue cells and then loaded with the fluid.

In option b) the liquid may be added to the scaffold immediately after the scaffold is seeded with cells, or there may if desired be a time delay between seeding the scaffold and applying the fluid to the scaffold.

In either option, several fluid applications may be made to the same scaffold over the course of the tissue growth, usually with removal of at least some of the fluid from the scaffold before the next application of fluid.

According to one embodiment of the second aspect of the invention there is provided a method of manufacturing a sampling device in which the scaffold
a) comprises fibres of a polymer comprising glycolide residues,
b) comprises fibres having a mean fibre diameter of between from about 1.2 to 4.0 microns, and
c) contains a fluid which is a liquid which reversibly thermally gels at about body temperature,
comprising loading the scaffold with the fluid.

In some forms of this embodiment of the second aspect of the invention the polymer is PGA.

In some forms of this embodiment of the invention the polymer content of the fibre comprises over 85% glycolide, over 90% glycolide, over 95% glycolide, or consists of 100% glycolide residues. The polymer may also comprise lactide residues.

According to another preferred embodiment of the second aspect of the invention there is provided a method of manufacturing a sampling device in which the scaffold
c) comprises fibres of a polymer comprising caprolactone residues,
d) comprises fibres having a mean fibre diameter of between from about 1.2 to 4.0 microns, and
e) contains a fluid which is a liquid which reversibly thermally gels at about body temperature,
comprising loading the scaffold with the fluid.

In some forms of this embodiment of the second aspect of the invention the polymer is PCL.

The manufacture of the sampling device can be performed within a laboratory or a manufacturing plant. Preferably, the method is performed in a treatment room, before applying the device to the wound, or in a tissue engineering laboratory, before seeding the device with cells.

It is generally preferred that in use as a wound sampling device the sampling device is secured to the body of the patient, generally by a backing layer which spans the sampling device, and which may bear at least one layer of pressure sensitive adhesive for the purpose.

Accordingly, in a third aspect of the present invention there is provided a conformable wound sampling dressing that comprises a backing layer with a wound-facing face, and at least one wound contact integer which in use lies in contact with the wound bed and with the wound-facing face of the backing layer.

The dressing is characterised in that the wound contact integer comprises a wound sampling device of the first aspect of the invention, which in use lies in contact with the wound bed.

According to one embodiment of this third aspect of the invention there is provided a sampling dressing in which the scaffold a) comprises fibres of a polymer comprising glycolide residues, b) comprises fibres having a mean fibre diameter of between from about 1.2 to 4.0 microns, and c) contains a fluid which is a liquid which reversibly thermally gels at about body temperature.

In some forms of this embodiment of the third aspect of the invention the polymer is PGA.

In some forms of this embodiment of the invention the polymer content of the fibre comprises over 85% glycolide, over 90% glycolide, over 95% glycolide, or consists of 100% glycolide residues. The polymer may also comprise lactide residues.

According to another preferred embodiment of the third aspect of the invention there is provided a sampling dressing in which the scaffold a) comprises fibres of a polymer comprising caprolactone residues, b) comprises fibres having a mean fibre diameter of between from about 1.2 to 4.0 microns, and contains a fluid which is a liquid which reversibly thermally gels at about body temperature.

In some forms of this embodiment of the third aspect of the invention the polymer is PCL.

The backing layer in the present wound sampling dressing preferably comprises a gas-permeable barrier layer which is capable of forming a relatively liquid-tight seal or closure over a wound.

In one embodiment of the third aspect of the invention, the wound contact integer consists essentially of the wound sampling device.

In one embodiment of the third aspect of the invention, the wound contact integer is separate from the rest of the sampling dressing before the sampling dressing is assembled in situ on the wound.

In another embodiment of the third aspect of the invention, the sampling device and/or the wound contact integer form part of the sampling dressing before its application to the wound.

In use, the sampling device, optionally as part of the wound contact integer of the sampling dressing, is applied to the wound bed.

As noted hereinbefore, the wound sampling device may be applied to the wound bed in a number of ways. Thus, a) the scaffold may be loaded with the fluid and the resultant sampling device placed in a wound, or b) the scaffold may be placed in a wound and then loaded with the fluid to form the sampling device in situ.

It is preferred that the scaffold is initially applied to the wound bed, and the fluid is applied afterwards, that is option b).

The fluid when applied is usually a relatively low viscosity liquid at room temperature, since this greatly eases the loading of the fluid into the scaffold before or after placing the scaffold on the wound bed, and the liquid can conform exactly to the shape of the wound and/or scaffold. Such a fluid may be applied by syringe, pipette or aerosol, or poured on from a bottle or other vessel, preferably with a spout or nozzle.

In option b), the liquid may be added to the scaffold immediately after the scaffold is placed in the wound, or there may if desired be a time delay between applying the scaffold and applying the fluid to the scaffold.

In option b), the liquid is usually added to the scaffold before the rest of the sampling dressing is placed over the wound.

Alternatively, there may if desired be means within the dressing to allow application of the fluid to the scaffold after the rest of the sampling dressing is placed over the wound, such as a window in the dressing backing layer with a peel-back resealable biocompatible plastics cover, allowing access to the sampling device and application of the fluid to the scaffold.

The rest of the sampling dressing (including the backing layer) is then applied over the wound and secured to the body of the patient, generally by the backing layer, which may bear at least one layer of pressure sensitive adhesive for the purpose.

In either option, several fluid applications may be made to the same scaffold over the course of the wound healing, usually with removal of at least some of the fluid from the scaffold before the next application of fluid. This may be effected as described hereinbefore in respect of the sampling device.

Thus, where, the fluid is reversibly switchable, by reverting to being a liquid on dilution or on being treated with a structure disruptant, or by being thermo-switchable, once a desired quantity of the desired markers have diffused, or where the markers are cell types that have migrated and proliferated, from the wound bed into the fluid in the scaffold, substantially all of the fluid may be converted to a liquid on being diluted, disrupted or cooled to room temperature.

Where appropriate, cooling of the gel may be achieved by means of a cooled sampling probe, placing a sample of gel on a cooled surface or in a refrigerator, or by any other known method of cooling, such as simply washing the scaffold with cool liquid (for example saline at 10-15° C.) to reverse the gelation and wash out the resultant liquid. The sampling gel containing the markers can be retrieved rapidly as a liquid from the scaffold. The liquid is then analysed in an assay.

The scaffold may be left in situ in the wound, and accessed by removing the rest of the dressing from over the scaffold or through a window, as described above, or removed from the wound, by first removing the rest of the dressing from over the scaffold. Fresh fluid may then be added to the scaffold in the wound sampling device, for example as described above.

The device, if removed from the wound, is then replaced, and if the rest of the device has been removed from over the scaffold, the rest of the device is replaced.

In another embodiment of the third aspect of the invention, the sampling device and/or the wound contact integer form part of the sampling dressing before its application to the wound.

The wound sampling device and/or the wound contact integer may be applied to the rest of the dressing, often the dressing backing layer in a number of ways. Thus, a) the scaffold may be loaded with the fluid and the resultant sampling device and/or the wound contact integer removably or irremovably attached to the rest of the dressing, or b) the scaffold and/or the wound contact integer may be removably or irremovably attached to the rest of the dressing and the scaffold then loaded with the fluid to form the sampling device in situ.

It is preferred that the scaffold is initially attached to the dressing, and the fluid is applied afterwards, that is option b).

In option b), the liquid is usually added to the scaffold before sampling dressing is placed over the wound. Alternatively, there may if desired be means within the dressing to allow application of the fluid to the scaffold after the sampling dressing is placed over the wound, such as a window in the dressing backing layer with a peel-back resealable biocompatible plastics cover, allowing access to the sampling device and application of the fluid to the scaffold.

In either option, several fluid applications may be made to the same scaffold over the course of the wound healing, usually with removal of at least some of the fluid from the scaffold before the next application of fluid. This may be effected as described hereinbefore in respect of the sampling device.

The fluid may be applied to and removed from the scaffold as described above for a scaffold which is separate from the rest of the dressing.

If it is desired to remove the dressing from the wound in order to recover the fluid from the scaffold, and the device and/or the wound contact integer is irremovably attached to the rest of the dressing, it will be necessary to remove and subsequently replace the dressing; if the device and/or the wound contact integer are removably attached, the dressing may be removed from over the wound, and the device and/or the wound contact integer removed from the rest of the dressing, reversing the process to replace the dressing.

The sampling dressing may be used in a wound that extends to at least the epidermis of the animal's skin, in a wound that extends to the dermis or the subcutaneous fat region of the animal's skin, in a wound that extends into the musculature of the animal, or in a wound that extends into the viscera of the animal.

In particular for shallower wounds, the wound contact integer which comprises the sampling device which in use is in contact with the wound bed may typically be or consist essentially of the sampling device.

Alternatively, a more suitable wound contact integer, in particular for deeper or cavity wounds comprises a conformable wound filler under the backing layer with a wound-facing face which in use lies in contact with the biodegradable and/or bioabsorbable sampling device.

The sampling device and the wound-facing face of the filler may be essentially coterminous. Alternatively, the wound-facing face of the filler may be smaller, preferably slightly smaller, than the opposing face of the sampling device, so that in use the sampling device at least partly surrounds the wound contact integer edges, and the sampling device lies in contact with the wound bed to its periphery.

The wound contact integer of the sampling dressing (that is, the sampling device and/or any wound filler) may optionally be compressible, and the volume of the integer in an uncompressed state before its application to the wound bed may be greater than the volume of the wound void at rest.

In this case, by securing the sampling dressing over the wound, pressure is applied to the compressible integer to press the sampling device onto and into intimate contact with the wound bed until the pressure is relieved by removing the sampling dressing from over the wound area. This results in a higher degree and rate of infiltration of the desired markers and/or cell types from the wound bed.

Preferably, the sampling dressing is secured to the body of the patient after its application to the wound such that the top face of the sampling device and/or any wound filler lies as close to flush as possible with the skin around the wound. This can result in a higher than average degree and rate of infiltration of the desired markers and/or cell types from the wound bed.

The wound filler as a component of the wound contact integer may be incompressible, or equally, less or more compressible as or than the biodegradable and/or bioabsorbable sampling device.

It may preferably be more compressible, so that in use there is less compression of the sampling device, but the latter is still pressed into intimate contact with the wound bed. This may be a preferred type of wound filler as it reduces the compression of the sampling device under the backing layer. Applying pressure to a compressible sampling device will tend to reduce its pore size. It is believed that this may have a negative effect on the degree and rate of infiltration of the desired markers into the sampling device, potentially leading to a restricted sampling performance.

Where (less preferably) the wound filler is less compressible than the sampling device, it may comprise a non-woven, woven or knitted textile fabric. This may be in the form of at least one cloth, layer or sheet, such as a gauze; at least one polymer film, layer sheet or membrane; or a at least one layer of a mesh, lattice, net or web; optionally bonded to each other and/or to the backing layer membrane with an adhesive or thermally.

Where more preferably the wound filler is more compressible than the sampling device, the preferred type of wound filler may comprise at least one conformable porous body, such as a foam. This may be in the form of at least one layer or sheet, optionally bonded to each other and/or to the backing layer membrane with an adhesive or thermally. The or each foam may be in a range of various forms, including closed- and open-cell foams.

It will be seen that the conformable wound filler under the backing layer, whether more or less compressible than the scaffold, may be comprise at least one conformable absorbent body, for examples a porous body, such as an open-cell foam, or a non-woven, woven or knitted textile fabric. Such a wound filler may absorb wound exudate in use through the scaffold or (less often) directly from the wound bed, if in contact with the latter, and will often expand as a result of such absorption, and further press the scaffold into intimate contact with the wound bed. Alternatively or additionally, a liquid, such as isotonic saline, may be deliberately added to the filler around or through the backing layer for that purpose.

In all embodiments of the third aspect of the present invention, the backing layer, all components of any wound filler, and the sampling device are all preferably mutually separate before application of the sampling dressing over a wound. The wound filler then preferably comprises more than one component cloth, layer, sheet, film or membrane so than the wound filler may be adjustably shimmed to the desired thickness, and more preferably comprises at least two foam layers or sheets.

The volume, and in practice the thickness, of the integer and/or sampling device is largely determined
by the volume of the wound void at rest, and in practice by the depth of the wound,
by the compressibility of the integer or sampling device, in turn determined by the structure of the sampling device and/or the wound contact integer, and by whether it is intended to allow an absorbent wound filler to swell with wound exudate or added fluid.

Broadly, the scaffold or filler needs to protrude above the skin surface around the wound, or if it is intended to allow an absorbent wound filler to swell, to be at least level with that surface.

For the suitable and preferred materials and structures of the scaffold and/or wound contact integer as so described hereinafter, examples of suitable depths of the scaffold and/or wound integer as a percentage of the depth of the wound are in the range of 100 to 150%, for example 100 to 130%, and 100 to 110%.

The volume of the wound void at rest (in practice the area and/or depth of the wound) to determine the thickness of the sampling device and/or the wound contact integer required may be determined by conventional invasive techniques. Such techniques include tracing the wound or a photograph thereof, and using a depth-gauge in the wound. However, non-invasive techniques, such as analysis of 3-D virtual photogrammetric images, such as in the Wound Measurement System™ from Eykona® are preferred.

As noted above, the backing layer in the present wound sampling dressing preferably comprises a gas-permeable barrier layer which is capable of forming a relatively liquid-tight seal or closure over a wound. In the sampling dressing, such a backing layer will prevent excessive water vapour loss or retention from the area of the wound while the sampling of the wound is taking place. In some embodiments of the invention such a sampling dressing backing layer is composed of biocompatible synthetic materials. Suitable materials include polymers, for example: polycellulose, polyurethane, polystyrene, polyimides, polyamides, resins, nylon, silicone, polyester, polyolefin for example polyethylene, polypropylene and polybutylene, and copolymers and mixtures thereof.

Silicone backing layers can be classified according to their permeability to vapour and air. Occlusive silicone sampling dressing backings are impermeable to vapour and air. Perforated silicone backing layers allow vapour and air exchange through the perforations whilst permeable silicone backing layers are vapour and air transmissible. In specific embodiments of the invention the backing layer is a silicone-based film, for example Cica-Care® (Smith & Nephew PLC).

As noted above, in one embodiment of the third aspect of the invention, the wound contact integer is separate from the rest of the sampling dressing before the sampling dressing is assembled in situ on the wound.

In another embodiment of the third aspect of the invention, the sampling device is separate from the rest of the sampling dressing before the sampling dressing is assembled in situ on the wound.

In a third embodiment of the third aspect of the invention, the sampling device and/or the wound contact integer form part of the sampling dressing before its application to the wound.

In use, the sampling device, optionally as part of the wound contact integer of the sampling dressing, is applied to the wound bed.

Where the wound contact integer and/or the sampling device is separate from the rest of the sampling dressing before the sampling dressing is assembled in situ on the wound, the rest of the sampling dressing is then applied over the wound and secured to the body of the patient.

Attachment of the sampling device or the wound contact integer removably or irremovably to the backing layer may be effected using a suitable adhesive, or other means of bonding. Alternatively, temporary or permanent adhesion of a spun scaffold sampling device may be effected by spinning, in particular electrospinning, the scaffold onto a layer of appropriate adhesive on the appropriate substrate; or, depending on a choice of materials for the sampling device, any spinning solvent and the appropriate substrate, the sampling device may be deposited by spinning, in particular electrospinning, and self-adhered removably or irremovably onto the surface of the substrate.

As noted above, some embodiments of the first aspect of the present invention (the sampling device) may be a wound sampling device that comprises a biodegradable porous scaffold which comprises a fluid and in use lies in contact with the wound bed. In other embodiments of the first aspect of the present invention the sampling device that comprises a biodegradable porous scaffold which comprises a fluid and on which is use tissue is grown in vitro.

All embodiments of the third aspect of the present invention (the sampling dressing) comprise a wound sampling device that comprises a biodegradable porous scaffold which comprises a fluid and in use lies in contact with the wound bed.

In all cases, the fluid provides a medium into which desired materials, such as markers may infiltrate. The length of time the device needs to be in contact with the wound bed or the tissue on it for enough infiltration into the scaffold of the desired materials (e.g. markers) from exudate and/or tissue to occur for the device to capture a sufficient sample of the materials for assay will depend on several factors. These include the viscosity of the fluid and the temperature in situ, the amount and distribution of other fluids in the scaffold, and how much and what type of information is required from the assay, which will depend in turn on the nature of the markers that are required for that information.

In the case of a wound sampling device, the contact time may be as little as 1 minute or so for a 'snapshot' sample of the markers present at that time, or as much as 48 hr to allow full diffusion/equilibration into the device to provide an aggregated sample.

In all cases, when capture of the desired markers is complete, the fluid containing the desired materials is removed from the wound bed and/or the incubation chamber.

As noted above, it is less preferred that the fluid in the scaffold (usually a gel) is not reversibly switchable (that is, substantially all of the fluid does not revert to a liquid on being diluted, disrupted or cooled to room temperature). Preferably, the fluid in the scaffold is a reversibly switchable gel, so that the gel containing the markers can be retrieved rapidly as a liquid from the scaffold.

The scaffold may be let in situ in the wound or incubation chamber or removed from the wound or incubation chamber for handling.

Where appropriate, switching may be achieved by diluting the gel below its critical gelation concentration: by the addition of an additive that disrupts the gel structure, such as an appropriate solvent or salt; or in the case of a thermo-switchable fluid, cooling the gel by means of a cooled sampling probe, placing a sample of gel on a cooled surface or in a refrigerator, or by any other known method of cooling, such as simply washing the scaffold with cool liquid (for example saline at 10-15° C.) to reverse the gelation and wash out the resultant liquid.

The liquid is then easily analysed in an assay.

A wound sampling device may often form part of a sampling dressing, in which the sampling device and/or a wound contact integer may be separate from, or removably or permanently attached to, a backing layer.

In all cases, the backing layer is peeled away before processing the sampling device. Where the sampling device and/or a wound contact integer are separate from a backing layer, the device may be left in situ or removed for processing. Where the sampling device and/or a wound contact integer are removably attached to a backing layer, the device may be separated from the backing layer and left in situ or removed for processing, or removed for processing attached to the backing layer. Where the sampling device and/or a wound contact integer are permanently attached to a backing layer, the device is removed for processing attached to the backing layer.

One embodiment of a fourth aspect of the present invention provides a method of manufacturing a wound sampling dressing of the third aspect of the invention, where the sampling device and/or the wound contact integer forms part of the sampling dressing before its application to the wound, which method comprises
a) attaching the sampling device or the wound contact integer removably or irremovably to the backing layer, or
b) attaching the scaffold or the wound contact integer without the fluid removably or irremovably to the rest of the wound contact integer or the backing layer, and then loading the scaffold reversibly or irreversibly with the fluid.

In option b), loading of the scaffold may be effected as described hereinbefore in respect of the scaffold in the production of the sampling device.

Attachment of the sampling device or the wound contact integer removably or irremovably to the backing layer may be effected using a suitable adhesive, or other means of bonding.

In option b), where appropriate, temporary or permanent adhesion of the spun sampling device may be effected by spinning, in particular electrospinning, the scaffold onto a layer of appropriate adhesive on the appropriate substrate.

Alternatively, depending on a choice of materials for the sampling device, any spinning solvent and the appropriate substrate, the sampling device may be deposited by spinning, in particular electrospinning, and self-adhered removably or irremovably onto the surface of the substrate.

Where the sampling device and/or the wound contact integer forms part of the sampling dressing before its application to the wound, the manufacture of the sampling dressing can be performed within a laboratory or a manufacturing plant, and the product, packaged and sterilised.

Alternatively, where the sampling device does not form part of the sampling dressing before its application to the wound, the dressing may be made up in situ, for example, at the site of the wound, for example in a treatment room, by applying the device to the wound, and then securing the backing layer, optionally having the rest of the wound facing integer, such as a wound filler, attached to it, to the patient.

Accordingly, another embodiment of a fourth aspect of the present invention provides a method of manufacturing a wound sampling dressing of the third aspect of the invention in situ on a wound, where the sampling device and/or the wound contact integer does not form part of the sampling dressing before its application to the wound, which method comprises
a) applying the sampling device or the wound contact integer to the wound, and
b) securing the backing layer over the sampling device or the wound contact integer to the skin of the patient, and optionally attaching it removably or irremovably to the wound contact integer or the sampling device.

According to one embodiment of the fourth aspect of the invention there is provided a method of manufacturing a sampling dressing in which the scaffold
a) comprises fibres of a polymer comprising glycolide residues,
b) comprises fibres having a mean fibre diameter of between from about 1.2 to 4.0 microns, and
c) contains a fluid which is a liquid which reversibly thermally gels at about body temperature.

In some forms of this embodiment of the fourth aspect of the invention the polymer is PGA.

In some forms of this embodiment of the invention the polymer content of the fibre comprises over 85% glycolide, over 90% glycolide, over 95% glycolide, or consists of 100% glycolide residues. The polymer may also comprise lactide residues.

According to another preferred embodiment of the fourth aspect of the invention there is provided a method of manufacturing a sampling dressing in which the scaffold
a) comprises fibres of a polymer comprising caprolactone residues,
b) comprises fibres having a mean fibre diameter of between from about 1.2 to 4.0 microns, and
c) contains a fluid which is a liquid which reversibly thermally gels at about body temperature.

In some forms of this embodiment of the fourth aspect of the invention the polymer is PCL.

According to a fifth aspect of the present invention there is provided a method of testing using the sampling device of the first aspect of the invention to monitor the physiological status of tissue and any associated pathologies, in which such a sampling device is applied to the tissue.

In one embodiment of the fifth aspect of the present invention, the method is a method of diagnosis, wherein the sampling device is a wound sampling device which, optionally as part of the wound contact integer of the sampling dressing, in use lies in contact with a wound bed.

In another embodiment of the fifth aspect of the present invention, the sampling device is a tissue engineering sampling device on which is use tissue is grown in vitro.

In the wound sampling embodiment, where the wound contact integer and/or the sampling device is separate from the rest of the sampling dressing before the sampling dressing is assembled in situ on the wound, the rest of the sampling dressing is then applied over the wound and secured to the body of the patient. Alternatively, where the sampling device and/or the wound contact integer form part of the sampling dressing before its application to the wound, the sampling dressing is then secured to the body of the patient.

The sampling dressing can be easily applied to monitor tissue the physiological status of for diagnosis a wide variety of biological conditions of an animal, including both humans and non-human animals.

The biological condition may be a wound, such as an acute wound, for example a surgical wound or a burn on the animal's skin, or a chronic wound, for example a diabetic ulcers or a venous leg ulcers. The sampling dressing may be used in a wound that extends to at least the epidermis of the animal's skin, in a wound that extends to the dermis or the subcutaneous fat region of the animal's skin, in a wound that extends into the musculature of the animal, or in a wound that extends into the viscera of the animal.

In one embodiment of the fifth aspect of the invention, the sampling dressing comprises a sampling device including fibres having a mean fibre diameter of between from about 1.2 to 4.0 microns, and wherein said fibres comprise a polymer comprising glycolide residues.

In another embodiment of the fifth aspect of the invention, the sampling dressing comprises a sampling device including fibres having a mean fibre diameter of between from about 1.2 to 4.0 microns, and wherein said fibres comprise a copolymer comprising glycolide and lactide residues.

In another embodiment of the fifth aspect of the invention there is provided a sampling device with a sampling device comprising fibres having a mean fibre diameter of between from about 1.2 to 4.0 microns, and wherein said fibres comprise a polymer comprising caprolactone residues.

In all the foregoing, the wound contact integer of the sampling dressing (and/or the sampling device within it) may be compressible, and the volume of the integer in an uncompressed state before its application to the wound bed may be greater than the volume of the wound void at rest.

By securing the sampling dressing over the wound pressure is applied to the compressible integer to press the sampling device onto and into intimate contact with the wound bed until the pressure is relieved by removing the sampling dressing from over the wound area.

This results in a higher degree and rate of infiltration, and hence the degree and rate of tissue the physiological status of over the wound bed.

Preferably, the sampling dressing is secured to the body of the patient after its application to the wound such that the top face of the sampling device and/or the wound contact integer lies as close to flush as possible with the skin in the wound area. This results in a higher than average degree and rate of infiltration, and accordingly a higher than average degree and rate of tissue the physiological status of over the wound bed, tending towards an optimal degree and rate.

The wound diagnosis sampling device of the first aspect of the present invention may also be used as a conformable wound dressing, in particular for treating chronic or non-healing problem wounds, such as venous leg ulcers, diabetic foot ulcers, pressure ulcers and burns, for example by hospital-based and community based wound care nurse specialists and tissue viability specialists.

The present biodegradable scaffold-fluid device which in use lies in contact with the wound bed facilitates and/or stimulates infiltration by granulation tissue and cells from the wound bed into the scaffold, thereby facilitating tissue regeneration and repair.

This leads to more efficient wound healing compared with conventional, non-biodegradable wound dressings (such as gauze, tape, films, polyurethane foams, hydrocolloids etc). This translates advantageously into earlier completion of patient therapy and thus savings to health systems.

Accordingly, in a sixth aspect of the present invention there is provided a conformable wound therapy dressing that comprises a biodegradable porous scaffold which in use lies in contact with the wound bed, characterised in that the scaffold comprises a fluid.

The dressing can be easily applied to facilitate and/or stimulate infiltration by granulation tissue and cells from the wound bed into the scaffold, thereby facilitating tissue regeneration and repair. The therapy dressing may be used in a wound that extends to at least the epidermis of the animal's skin, in a wound that extends to the dermis or the subcutaneous fat region of the animal's skin, in a wound that extends into the musculature of the animal, or in a wound that extends into the viscera of the animal.

The present wound therapy dressing preferably comprises a backing layer, in particular in the form of a gas-permeable barrier layer which is capable of forming a relatively liquid-tight seal or closure over the wound.

Accordingly, in a preferred embodiment of the sixth aspect of the present invention there is provided a conformable wound therapy dressing that comprises a backing layer with a wound-facing face, and at least one wound contact integer which in use lies in contact with the wound bed, characterised in that the wound contact integer comprises a biodegradable porous scaffold which in use lies in contact with the wound bed and comprises a fluid.

To further facilitate tissue regeneration and repair, the wound contact integer may comprise a therapeutic agent, such as an antimicrobial agent, such as silver, iodine or chlorhexidine, or an agent that improves scar resolution and/or prevents scar formation, for example: insulin, vitamin B, hyaluronic acid, mitomycin C, growth factors (TGF [beta]), cytokines, corticosteroids and/or agents that promote re-epithelialisation.

Where appropriate, the substance can be provided within the fluid in the scaffold. Additionally or alternatively it may be provided in the fibres of a fibrous scaffold by incorporating it in a scaffold polymer spinning solution prior to fibre formation, or the substance may be associated with the fibre post-formation.

Suitable and preferred materials, structures and methods of preparation of the therapy dressing of the sixth aspect of the present invention are as so described for the sampling device of the first aspect of the present invention and the sampling dressing of the third aspect of the present invention.

In preferred embodiments of the sixth aspect of the invention, the sampling device fluid is or comprises one or more thermo-switchable gel materials. Such materials switch from a liquid to a gel at a given temperature or over a given temperature range. Preferred materials include those that switch from a liquid below a given temperature or temperature range to a gel above that temperature or temperature range. Preferred materials include those that switch, and in particular thermally gel, at or near normal body temperature for the human or animal patient. Suitable materials include those that switch reversibly through a given temperature or temperature range.

Such materials are preferred because of the convenience in use which they provide.

When in the porous scaffold of the device in situ on a human or animal patient, it is preferred that the fluid is a gel or other similar material so that it can function as a medium into which desired cell types may migrate and proliferate, from the wound bed, but that the fluid does not leak from the scaffold. However, it is preferred that some, if not substantially all, of the fluid is a liquid at room temperature, since this greatly eases the loading of the fluid into the scaffold before the use of the device on the wound bed.

Suitable reversible thermo-switchable materials include those based on poly(hydroxyalkanoic acids), such as poly(L-lactic acid), poly(D-lactic acid), poly(D/L-lactic acid), poly(glycolic acid), poly(glycolic acid-co-lactic acid), polydioxanones, polycaprolactone, and those based on poly(alkylene oxides), such as poly(ethylene oxide) (PEO), also known as poly(ethylene glycol) (PEG), poly(propylene oxide) and poly(butylene oxide), and copolymers and mixtures thereof.

In preferred embodiments of the invention the material comprises a copolymer of a glycolide and/or a lactide and/or other suitable hydroxy acids and/or a poly(ethylene glycol) (PEG).

Examples of suitable copolymers include triblock copolymers that contain poly(lactide-co-glycolide) (PLGA) random copolymer end blocks and a poly(ethylene glycol) (PEG) homopolymer central block. Any such triblock copolymer may be represented by the following formula: PLGA-PEG-PLGA. Typical molecular weights for the PLGA end blocks are in the range 1,500-3000. The molecular weight for the central PEG block is typically 1,000 or 1,500.

The fluid comprises an aqueous solution of the copolymer, typically at 10-50 w/v %.

It is believed that gelation of the triblock copolymer solution is a physical change brought about by changes in polymer solubility as the temperature is changed. At temperatures below the lower consolute solution temperature (LCST) of the PLGA polymer blocks, the triblock copolymer is soluble in water. As the temperature is increased above the LCST, hydrogen bonding between the water and the PLGA blocks is disrupted and the polymer becomes increasingly insoluble. If the solution concentration is high enough, a gel is formed when collapse of the PLGA blocks forms micelles comprising insoluble polymer microdomains surrounded by the still-soluble PEG polymer. The process is thermally reversible.

Again, the fluid is often contained in at least part of the accessible and otherwise empty interstices between the fibres of the scaffold, preferably in more than 50% of the interstices, more preferably between 75 and 100%, and most preferably in substantially all of the interstices.

The fluid may be uniformly distributed in the scaffold, or the majority of the fluid may lie towards the periphery of the scaffold, with the core of the scaffold being substantially free of fluid. It is preferred that some, if not substantially all of the fluid is uniformly distributed over the periphery of the scaffold, since that part of the scaffold comprises its interface with the wound bed which must be crossed by the desired markers.

Since the fluid provides a growth medium for surrounding cells, it may contain a cell nutrient, a therapeutic agent, such as an antimicrobial agent, such as silver, iodine or chlorhexidine, or an agent that improves scar resolution and/or prevents scar formation, for example: insulin, vitamin B, hyaluronic acid, mitomycin C, growth factors (TGF[beta]), cytokines or corticosteroids, and/or agents that promote cell growth and re-epithelialisation.

Where appropriate, the substance can be provided within a scaffold polymer spinning solution prior to fibre formation. Additionally or alternatively the substance may be associated with the fibre post-formation.

In a preferred embodiment of the sixth aspect of the present invention there is provided a therapy dressing with a scaffold comprising fibres having a mean fibre diameter of between from about 1.2 to 4.0 microns, and wherein said fibres comprise a polymer comprising glycolide residues. In some forms of this embodiment of the invention the polymer content of the fibre comprises over 85% glycolide, over 90% glycolide, over 95% glycolide, or consists of 100% glycolide residues. The polymer may also comprise lactide residues.

Poly(glycolic acid) (PGA), also referred to as polyglycolide, and copolymers of glycolic acid (GA) with other hydroxyalkanoic acids or internal esters, such as lactic acid (LA) or caprolactone (CL), are biodegradable, thermoplastic polymers. PGA may be prepared from GA by means of polycondensation or ring-opening polymerisation of glycolide.

Copolymers of GA with other hydroxyalkanoic acids or internal esters may be prepared from glycolic acid (GA) and the other acid by polycocondensation and/or ring-opening copolymerisation. PGA and GA copolymers are characterised by hydrolytic instability owning to the presence of the ester linkage in the backbone, and thus when exposed to physiological conditions, they are degraded by random hydrolysis.

The degradation products, glycolic acid and/or the hydroxyalkanoic acids or internal ester are non-toxic and can enter the tricarboxylic acid cycle after which they are excreted as water and carbon dioxide. The polymers have been shown to be completely resorbed by an organism in a time frame of four weeks to six months.

According to another preferred embodiment of the invention there is provided a dressing with a scaffold comprising fibres having a mean fibre diameter of between from about 1.2 to 4.0 microns, and wherein said fibres comprise a polymer comprising caprolactone residues.

Polycaprolactone (PCL) and copolymers of caprolactone (CL) with other hydroxyalkanoic acids or internal esters are also biodegradable, thermoplastic polymers. PCL may be prepared from CL by means of ring-opening.

Suitable and preferred materials for the scaffold may be solvent spun using appropriate solvents, such as dimethylformamide, methylene chloride, chloroform, dichloromethane, acetonitrile, methanol, N-methylpyrolidone, hexafluoroisopropanol and dimethyl sulphoxide.

Such solvents may contain appropriate additives, such as sodium chloride, sodium acetate, magnesium chloride, potassium dihydrogen phosphate, potassium iodate and potassium phosphate calcium carbonate, calcium phosphate and calcium lactate, in solution form or in nanoparticulate forms. They may also contain any other additives, solvents, polymers, bioactives, pharmaceutical agents, metals, metal oxides or cells or cellular components known to one skilled in the art that can be integrated into a spun format.

In a preferred embodiment of the sixth aspect of the present invention there is provided a conformable wound dressing that comprises a backing layer with a wound-facing face, and at least one wound contact integer which in use lies in contact with the wound bed, characterised in that the wound contact integer comprises a biodegradable porous scaffold which in use lies in contact with the wound bed and comprises a fluid.

Such a wound dressing preferably comprises a backing layer in the form of a gas-permeable barrier layer which is capable of forming a relatively liquid-tight seal or closure over a wound. Such a backing layer will prevent excessive water vapour loss or retention from the area of the wound.

In one form of this preferred embodiment of the sixth aspect of the invention, the wound contact integer consists essentially of the scaffold containing the fluid.

In one form of this embodiment, the wound contact integer is separate from the rest of the dressing before the dressing is assembled in situ on the wound.

In another form of this embodiment, the scaffold containing the fluid is separate from the rest of the dressing before the dressing is assembled in situ on the wound.

In a further form of this embodiment, the scaffold containing the fluid and/or the wound contact integer form part of the dressing before its application to the wound.

In use, the scaffold containing the fluid, optionally as part of the wound contact integer of the dressing, is applied to the wound bed.

Where the wound contact integer and/or the scaffold containing the fluid is separate from the rest of the sampling dressing before the dressing is assembled in situ on the wound, the rest of the dressing (including the backing layer) is then applied over the wound.

It is then secured to the body of the patient, generally by the backing layer, which may bear at least one layer of pressure sensitive adhesive for the purpose.

Alternatively, where the scaffold containing the fluid and/or the wound contact integer form part of the sampling dressing before its application to the wound, the dressing is then secured to the body of the patient. This again generally effected by the backing layer, which may bear at least one layer of pressure sensitive adhesive for the purpose.

A seventh aspect of the present invention provides a method of manufacturing a wound therapy dressing of the sixth aspect of the invention, which comprises loading the scaffold reversibly or irreversibly with the fluid.

Suitable and preferred materials, structures and methods for this seventh aspect of the present invention are as so described for the process of the second aspect of the present invention (sampling device) and the process of the fourth aspect of the present invention (sampling dressing).

According to one embodiment of the seventh aspect of the invention there is provided a method of manufacturing a wound dressing in which the scaffold
a) comprises fibres of a polymer comprising glycolide residues,
b) comprises fibres having a mean fibre diameter of between from about 1.2 to 4.0 microns, and
c) contains a fluid which is a liquid which thermally gels at about body temperature,
comprising loading the scaffold with the fluid.

In some forms of this embodiment of the seventh aspect of the invention the polymer is PGA.

In some forms of this embodiment of the invention the polymer content of the fibre comprises over 85% glycolide, over 90% glycolide, over 95% glycolide, or consists of 100% glycolide residues. The polymer may also comprise lactide residues.

According to another preferred embodiment of the seventh aspect of the invention there is provided a method of manufacturing a wound dressing in which the scaffold
a) comprises fibres of a polymer comprising caprolactone residues,
b) comprises fibres having a mean fibre diameter of between from about 1.2 to 4.0 microns, and
c) contains a fluid which is a liquid which reversibly thermally gels at about body temperature,
comprising loading the scaffold with the fluid.

In some forms of this embodiment of the seventh aspect of the invention the polymer is PCL.

The manufacture of the scaffold containing fluid can be performed within a laboratory or a manufacturing plant. Alternatively, the method can be performed in a treatment room, before applying the device to the wound.

One embodiment of an eighth aspect of the present invention provides a method of manufacturing a wound therapy dressing of the sixth aspect of the invention, where the scaffold containing the fluid and/or the wound contact integer forms part of the dressing before its application to the wound, which method comprises
a) attaching the scaffold containing the fluid or the wound contact integer removably or irremovably to the backing layer, or
b) attaching the scaffold or the wound contact integer without the fluid removably or irremovably to the rest of the wound contact integer or the backing layer, and then loading the scaffold reversibly or irreversibly with the fluid.

In option b), loading of the scaffold may be effected as described hereinbefore in respect of the scaffold in the production of the dressing.

Attachment of the scaffold containing the fluid or the wound contact integer removably or irremovably to the backing layer may be effected using a suitable adhesive, or other means of bonding.

In option b), where appropriate, temporary or permanent adhesion of the spun sampling device may be effected by spinning, in particular electrospinning, the scaffold onto a layer of appropriate adhesive on the appropriate substrate.

Alternatively, depending on a choice of materials for the scaffold, any spinning solvent and the appropriate substrate, the scaffold may be deposited by spinning, in particular electrospinning, and self-adhered removably or irremovably onto the surface of the substrate.

Where the scaffold containing the fluid and/or the wound contact integer forms part of the dressing before its application to the wound, the manufacture of the dressing can be performed within a laboratory or a manufacturing plant, and the product, packaged and sterilised.

Alternatively, where the scaffold containing the fluid does not form part of the sampling dressing before its application to the wound, the dressing may be made up in situ, for example, at the site of the wound, for example in a treatment room, by applying the scaffold containing the fluid to the wound, and then securing the backing layer, optionally having the rest of the wound facing integer, such as a wound filler, attached to it, to the patient.

Accordingly, another embodiment of the eighth aspect of the present invention provides a method of manufacturing a wound dressing of the sixth aspect of the invention in situ on a wound, where the scaffold containing the fluid and/or the wound contact integer does not form part of the sampling dressing before its application to the wound, which method comprises
a) applying the scaffold containing the fluid or the wound contact integer to the wound, and
b) securing the backing layer over the scaffold containing the fluid or the wound contact integer to the skin of the patient, and optionally attaching it removably or irremovably to the wound contact integer or the scaffold containing the fluid.

According to one embodiment of the eighth aspect of the invention there is provided a method of manufacturing a dressing in which the scaffold
a) comprises fibres of a polymer comprising glycolide residues,
b) comprises fibres having a mean fibre diameter of between from about 1.2 to 4.0 microns, and
c) contains a fluid which is a liquid which thermally gels at about body temperature.

In some forms of this embodiment of the eighth aspect of the invention the polymer is PGA.

In some forms of this embodiment of the invention the polymer content of the fibre comprises over 85% glycolide, over 90% glycolide, over 95% glycolide, or consists of 100% glycolide residues. The polymer may also comprise lactide residues.

According to one embodiment of the eighth aspect of the invention there is provided a method of manufacturing a dressing in which the scaffold
d) comprises fibres of a polymer comprising caprolactone residues,
e) comprises fibres having a mean fibre diameter of between from about 1.2 to 4.0 microns, and f) contains a fluid which is a liquid which thermally gels at about body temperature.

In some forms of this embodiment of the eighth aspect of the invention the polymer is PCL.

The present invention also relates to a method of treatment using the dressing of the sixth aspect of the invention, which method of treatment can be easily applied to a variety of wounds, and including acute and chronic wounds, to help combat infections and/or any underlying pathologies.

Accordingly, a ninth aspect of the present invention provides a method of wound treatment using the dressing of the sixth aspect of the invention, in which the scaffold containing the fluid, optionally as part of the wound contact integer of the sampling dressing, is applied to the wound bed.

Where the wound contact integer and/or the scaffold containing the fluid is separate from the rest of the dressing before the dressing is assembled in situ on the wound, the rest of the dressing is then applied over the wound and secured to the body of the patient. Alternatively, where the scaffold containing the fluid and/or the wound contact integer form part of the dressing before its application to the wound, the dressing is then secured to the body of the patient.

The dressing can be easily applied to treat a wound, and including an acute or chronic wound on the animal's skin. The dressing may be used as appropriate in a wound that extends to at least the epidermis of the animal's skin, in a wound that extends to the dermis or the subcutaneous fat region of the animal's skin, in a wound that extends into the musculature of the animal, or in a wound that extends into the viscera of the animal.

In one embodiment of the ninth aspect of the invention, the dressing comprises a scaffold including fibres having a mean fibre diameter of between from about 1.2 to 4.0 microns, and wherein said fibres comprise a polymer comprising glycolide residues.

In another embodiment of the ninth aspect of the invention, the dressing comprises a scaffold including fibres having a mean fibre diameter of between from about 1.2 to 4.0 microns, and wherein said fibres comprise a copolymer comprising glycolide and lactide residues.

In another embodiment of the ninth aspect of the invention, the dressing comprises a scaffold including fibres having a mean fibre diameter of between from about 1.2 to 4.0 microns, and wherein said fibres comprise a polymer comprising caprolactone residues.

We have found that in scaffolds applied in this way the degree and rate of infiltration, and hence the degree and rate of tissue regeneration and repair over the wound bed, may be enhanced.

We have surprisingly found that this may be achieved by a wound therapy dressing which applies pressure to a compressible scaffold that is, or is the underside of, a wound contact integer in such a dressing, and through it to the wound bed.

This is the more surprising since a scaffold having fibres of a small diameter will generally also be characterised by a small pore size, and applying pressure to a compressible porous scaffold will tend to reduce the pore size. It is believed in the art that this will have a negative effect on the degree and rate of migration of the cells into the scaffold, potentially leading to a restricted regeneration of replacement tissue around the periphery of the scaffold, with the core of the scaffold being substantially acellular.

In all the foregoing, the wound contact integer of the dressing (and/or scaffold containing the fluid within it) may be compressible, and the volume of the integer in an uncompressed state before its application to the wound bed may be greater than the volume of the wound void at rest.

By securing the dressing over the wound, pressure is applied to the compressible integer to press the sampling device onto and into intimate contact with the wound bed until the pressure is relieved by removing the sampling dressing from over the wound area. This results in a higher degree and rate of infiltration, and hence a higher degree and rate of tissue regeneration and repair over the wound bed.

Preferably, the dressing is secured to the body of the patient after its application to the wound such that the top face of the scaffold and/or the wound contact integer lies as close to flush as possible with the skin in the wound area. This results in a higher than average degree and rate of infiltration, and accordingly a higher than average degree and rate of tissue regeneration and repair over the wound bed.

For scaffolds and/or wound contact integers as so described hereinafter, examples of suitable depths of the scaffold and/or wound integer as a percentage of the depth of the wound are in the range of 100 to 150%, for example 100 to 130%, and 100 to 110%.

The volume of the wound void at rest (in practice the area and/or depth of the wound) used to determine the thickness of the sampling device and/or the wound contact integer required may be determined by conventional invasive techniques, such as tracing the wound or a photograph thereof, and using a depth-gauge in the wound.

However, non-invasive techniques, such as analysis of 3-D virtual photogrammetric images, such as in the Wound Management System™ from Eykona® are preferred.

The present invention is illustrated by the following figures and examples:

FIG. 1: Cryogenic scanning electron microscopy (cryo-SEM) image showing a fractured cross-section through a sampling device of the first aspect of the invention, FIGS. 2a, 2b, 2c, 2d: Isometric cross-sections through wound sampling dressings of the sixth aspect of the invention.

Figure 3:
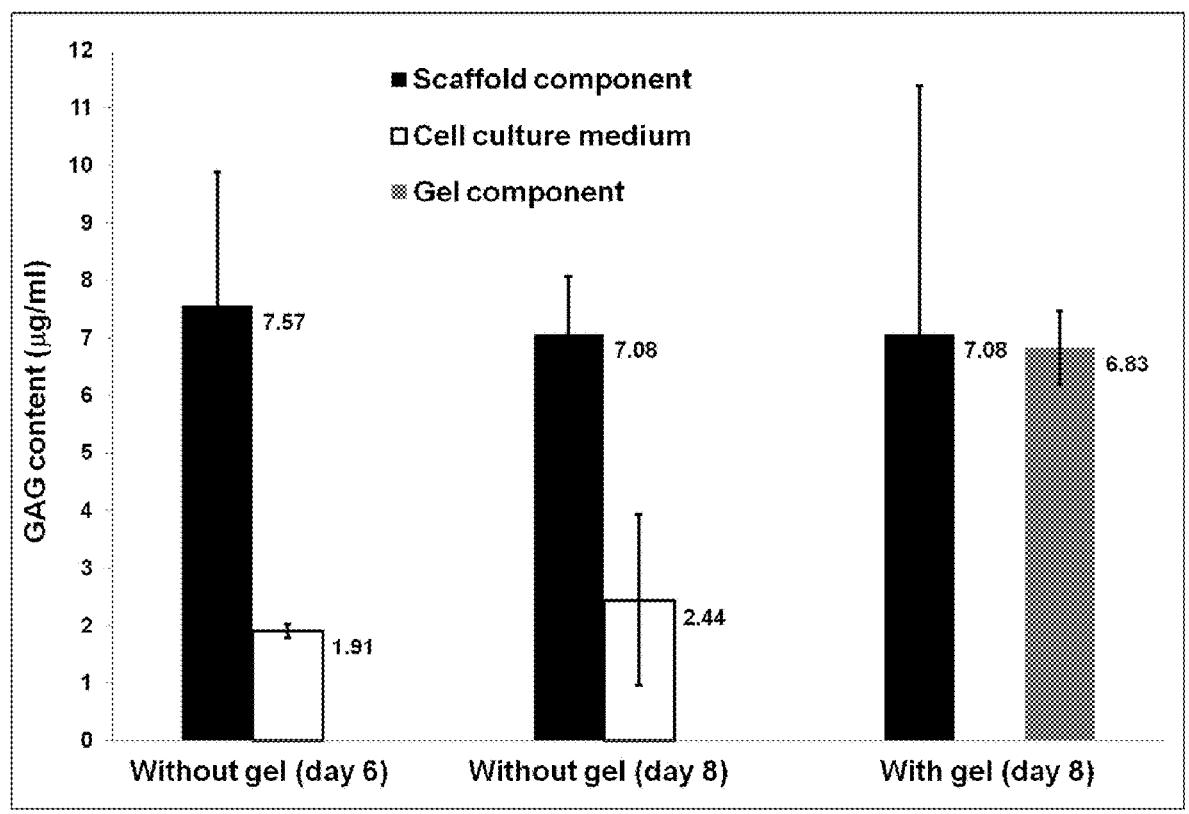

FIG. 3: Quantitative results of the biochemical analysis of glycosaminoglycan (GAG) produced by cells cultured and sampled in vitro described in Example 3.

Referring to FIG. 1, this shows a PLGA-PEG-PLGA hydrogel entirely penetrating the interstices formed by the fibres of an electrospun PGA scaffold. (The scaffold can be seen protruding from the bottom of the fractured composite sampling device).

Referring to FIGS. 2a, 2b, 2c and 2d, each dressing 1 is shown with its wound facing surface 2 uppermost. Each dressing 1 comprises a conformable backing layer in the form of a gas-permeable biocompatible synthetic polymer film barrier layer 3 which is capable of forming a relatively liquid-tight seal or closure over a wound, here a polyurethane or silicone backing layer.

On the wound facing surface 4 of the conformable backing layer 3, is mounted a wound contact integer which consists essentially of a wound sampling device 5. The wound sampling device comprises a biodegradable porous scaffold comprising a fluid, 8 in FIGS. 2a and 2c and 6 in FIGS. 2b and 2d, which in use lies in contact with tissue to be sampled, usually a wound bed.

The scaffold 6 or 8 is here an electrospun PGA scaffold, the interstices formed by the fibres of the scaffold 6 or 8 being at least partly penetrated by a thermo-reversible PLGA-PEG-PLGA sampling hydrogel in the form of a relatively low viscosity liquid at room temperature which reversibly thermally gels at about body temperature.

Figure 2A:
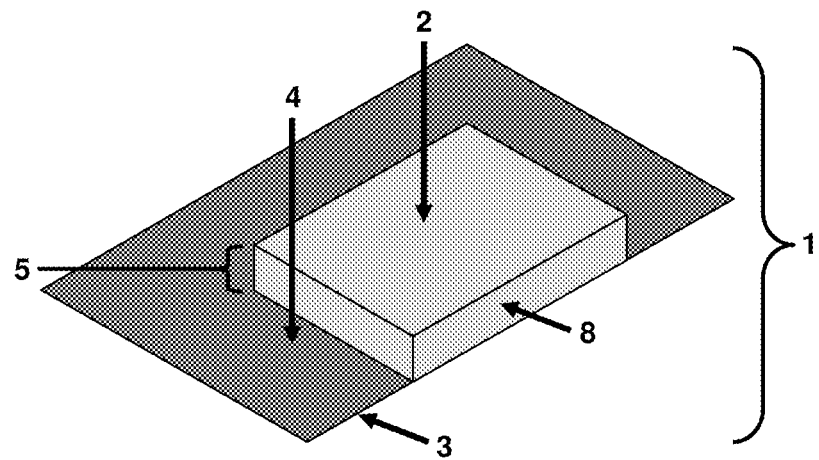
Figure 2B:
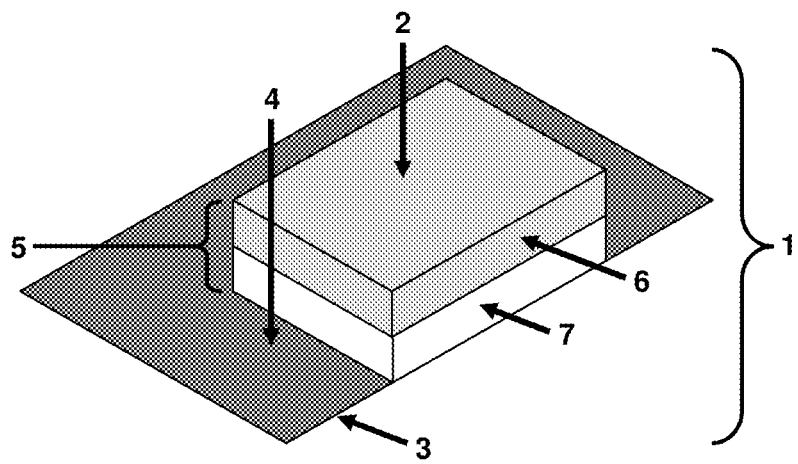
Figure 2C:
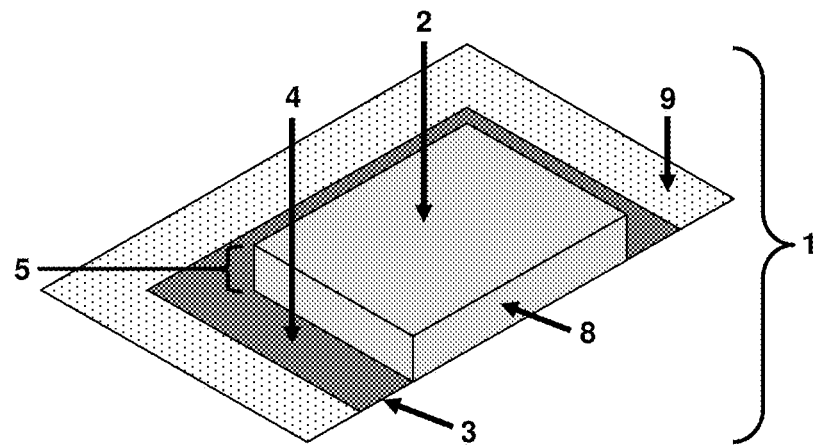

In the forms of the dressings 1 shown in FIGS. 2a and 2c the scaffold 8 comprising the fluid is mounted directly on the wound facing surface 4 of the conformable backing layer 3. In the forms shown in FIGS. 2b and 2d the scaffold 6 comprising the liquid is mounted on a porous body such as a foam or textile 7 which contains the same liquid as in the scaffold 6, and which in turn is mounted directly on the wound facing surface 4 of the conformable backing layer 3.

Figure 2D:
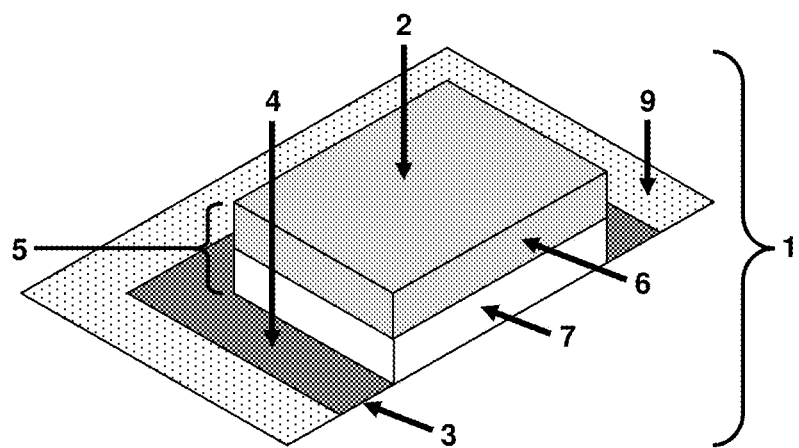

In FIGS. 2c and 2d, the periphery of the wound facing surface 4 of the conformable backing layer 3 is covered with a layer of a pressure sensitive adhesive 9 for the purpose of securing the dressing to the body of the patient.

In one form of each of these dressings 1 the wound facing surface of the wound contact integer 5 is covered with at least one layer of a mesh, lattice, net or web, such as a gauze, which is optionally bonded to the wound contact integer 5 and/or the conformable backing layer 3.

In another form of each of these dressings 1, the sampling device/the wound contact integer 5 does not form part of the sampling dressing 1 before its application to the wound, but the dressing 1 is assembled in situ on the wound, starting with the sampling device 5, optionally as part of the wound contact integer of the sampling dressing 1 being applied to the wound bed with the scaffold 6 or 8 being in contact with the wound bed.

In use, each dressing 1 is placed or assembled on the patient with its wound facing surface 2 towards a wound on a patient, such that the scaffold 6 or 8 comprising the liquid lies in contact with the wound bed, and it is preferably secured to the patient by its conformable backing layer 3 which forms a relatively liquid-tight seal or closure over a wound on the patient.

The fluid in the scaffold 6 or 8 which is a relatively low viscosity liquid at room temperature reversibly thermally gels at about body temperature in the wound, and the desired materials, such as markers infiltrate the gel from the wound bed. (Such markers may be for example, a microbial product, a part of the microbial cell contents, microbial cells; or a substance or cell associated with a living human or animal body's response to a microbe, a wound or an endocrine or metabolic condition.)

The dressing 1 is left in situ in the wound for an appropriate period (according to medical requirements) before the gel is cooled, optionally in situ before being removed from the wound, in order to reverse the gelation and convert the sample to a relatively low viscosity liquid. The liquid is then easily analysed in an assay, requiring little or no further processing. Where appropriate, recovery of the gel may be achieved by cooling the gel, for example in situ by means of a cooled sampling probe, placing a sample of gel on a cooled surface or in a refrigerator, or by any other known method of cooling, such as simply washing the scaffold in situ or ex situ with cool liquid (for example saline at 10-15° C.)

Features of FIG. 3 are described in Example 3.

EXAMPLE 1

Preparation of an Electrospun Fibrous Scaffold

Poly(glycolic acid) (PGA) was used to prepare a 9.25 w/w % solution of PGA in 1,1,1,3,3,3-hexafluoropropan-2-ol (HFIP). PGA and HFIP were weighed into a glass vial and left until dissolved. Prior to electrospinning, the solution of PGA in HFIP was filtered through a 10 µm polypropylene filter into a polypropylene syringe. The resulting clear pale yellow solution was then loaded into a syringe pump. The syringe exit was connected to a HFIP-resistant flexible plastic tube, which then split into two tubes. These tubes connected to two flat-ended 21 gauge steel needles, which were supported in a needle arm which could be made to traverse by means of a motor.

The pair of needles was aligned perpendicularly with respect to the rotational axis of the earthed 50 mm diameter, 200 mm long steel mandrel and the needle tip to mandrel separation distance was set to 120 mm. The syringe pump was set to dispense polymer solution at 0.04 mLmin$^{-1}$ per needle. The mandrel was completely covered in a sheet of non-stick release paper and rotated at 50 rpm for the duration of the collection process by means of a motor. The experiment was conducted at 21±1° C.

When the needles were charged to a potential difference of 10 kV relative to the mandrel, electrospun fibres were then formed from the solution of PGA delivered to the needle tips, which collected on the paper-covered mandrel to form a non-woven scaffold material. After sufficient scaffold had collected, the voltage generator was switched off and then the scaffold sheet was removed from the mandrel and dried overnight in a vacuum oven at room temperature to remove any residual solvent.

The thickness of the fibrous scaffold sheet was measured to be 100-110 µm by callipers. The mean fibre diameter of the PGA fibres in the scaffold was measured from SEM images to be 2.48 µm with a standard deviation of 0.32 µm. Capillary flow porometry was used to measure the median and modal pore diameters, which were 6.43 µm and 6.04 µm, respectively.

EXAMPLE 2

Use of the Electrospun Scaffold Component of Example 1 with a Thermo-Switchable Gel to Form a Sampling Device Poly(lactic acid-co-glycolic acid)-poly(ethylene glycol)-poly(lactic acid-co-glycolic acid) (PLGA-PEG-PLGA) triblock copolymers were synthesised by bulk ring opening polymerisation of DL-lactide (LA) and glycolide (GA) monomers onto poly(ethylene glycol) (PEG) in the presence of stannous octoate catalyst under dry nitrogen atmosphere.

PEG (number average molecular weight of 1000) was weighed into a two-neck round bottom flask and heated under vacuum for three hours at 120° C. The GA and LA monomers were then added and the mixture heated at 150° C. under a argon atmosphere for 30 minutes (LA/GA molar ratio=1.58). Stannous octoate catalyst was then added and the reaction allowed to proceed for eight hours under a static argon atmosphere. On completion of the reaction, the flask was gently rinsed using cold distilled water to remove unreacted monomer, before adding hot distilled water (60° C.). The flask was allowed to cool to 5° C. while stirring, and then stirred at 5° C. overnight.

The dissolved reaction products were then precipitated by placing the flask in an 80° C. water bath for two hours, after which the supernatant was decanted.

The dissolution and precipitation step was repeated, before the precipitate was freeze-dried for two days in order to obtain a light amber viscous polymer. The number average molecular weight was determined to be 3338 by gel permeation chromatography (GPC), LA/GA was measured to be 1.51 by $^1$H nuclear magnetic resonance spectroscopy (NMR), and the sol-gel transition temperature was determined to be 16° C. from rheological measurements.

A second triblock copolymer was also prepared using a similar method to the first, but using PEO with a number average molecular weight of 1500 and a LA/GA molar ratio of 2.5 instead. The number average molecular weight was determined to be 4684 by GPC, LA/GA was measured to be 2.39 by $^1$H NMR, and the sol-gel transition temperature was determined to be 31° C. from rheological measurements. The two triblock copolymers were blended in the ratio of 27:73 (first:second) to obtain a 35 w/v % mixture with a sol-gel transition temperature of 27.5° C.

This solution at 4° C. was added to discs of the electrospun bioresorbable scaffold described in Example 1, which were maintained at 32° C. (a typical skin temperature). The triblock copolymer solution penetrated the scaffold and then formed a gel as its temperature rose from 4° C. to 32° C.

The scaffold-gel composites were mounted on a sample holder and then flash frozen in liquid nitrogen prior to analysis by cryogenic scanning electron microscopy (cryo-SEM). Images of fractured cross-sections of the composites were recorded, a representative sample of which is shown in FIG. 1. It is clear that the PLGA-PEG-PLGA hydrogel entirely penetrating the interstices formed by the fibres of the electrospun PGA scaffold (PGA fibres can be seen protruding from the bottom of the fractured composite).

EXAMPLE 3

Quantitative Biochemical Analysis of Glycosaminoglycan (GAG) Produced by Cells Cultured and Sampled In Vitro Using a Sampling Device of the First Aspect of the Invention.

Neonatal human dermal fibroblast (HDFn) cells were expanded in vitro at 32° C. (5% $CO_2$). 3.5×10$^5$ HDFn cells were seeded into 13 mm discs of the electrospun bioresorbable scaffold described in Example 1.

Dulbecco's Modified Eagle Medium (DMEM) supplemented with 10 v/v % foetal bovine serum (FBS) and 1 v/v % antibiotic/antimycotic (Ab/Am) was used as the cell culture medium and refreshed every other day. In a control sample, the cells were cultured for 8 days.

In a test sample, the same cells were cultured in the same system for 6 days. The PLGA-PEG-PLGA triblock copolymer blend described in Example 2 supplemented with 10 v/v % FBS and 1 v/v % Ab/Am was added to the culture system for a final 2 culture days, and formed a gel at the culture temperature.

After culturing the cells with and without gel present, the levels of glycosaminoglycan (GAG) present in the cell-containing scaffold, culture medium and sampled gel was quantitatively assessed using a 1,9-dimethylmethylene blue assay.

The results of the analysis are shown in FIG. 3, from which it can be seen that the sampled gel from the scaffold & gel experiment (right-hand column set) contained much higher levels of GAG than was detected in the culture medium of the control experiments (identical except for the presence of the sampling gel). The GAG level in the gel was comparable to the level detected within the scaffolds containing the cultured cells. The two control experiments show levels of GAG measured in the cell culture scaffold and surrounding cell culture medium at six days (left-hand column set; the same time point at which gel was introduced to the scaffold & gel experiment) and eight days (middle column set; the same time point when the gel was sampled from the scaffold & gel experiment).

GAG is an important extracellular matrix (ECM) component, released by fibroblast cells as they form new tissue during the wound healing process. Therefore these experiments demonstrate that the hydrogel is capable of retaining biological information about the status of new tissue formation.

The invention claimed is:

1. A sampling device for capturing a biological marker, the sampling device comprising:
    a biodegradable porous scaffold comprising a polymer fibre selected from the group consisting of poly(L-lactic acid) (PLLA), poly(D-lactic acid) (PDLA), poly (D/L-lactic acid) (PDLLA), poly(glycolic acid) (PGA), poly(lactic acid-co-glycolic acid) (PLGA), polycaprolactone (PCL), polydioxanone (PDO), poly(trimethylene carbonate) (PTMC), poly(ethylene glycol) (PEG), and mixtures thereof, wherein the polymer fibre has a mean fibre diameter of from about 1.2 to 4.0 microns, wherein the biodegradable porous scaffold is configured to, in use, lie in contact with tissue to be sampled; and
    a fluid loaded into the scaffold,
    wherein the fluid consists of an aqueous solution of one or more thermo-switchable gel materials, which will thermally gel from a liquid below a given temperature or temperature range to a gel above that temperature or temperature range, wherein each of the one or more thermo-switchable gel materials is a triblock copolymer which contains (i) a poly(lactic acid-co-glycolic acid) (PLGA) random copolymer end blocks and a poly(ethylene glycol) (PEG) homopolymer central block, or (ii) a poly(ethylene oxide) (PEO) random copolymer and a poly(propylene oxide) (PPO) homopolymer central block,
    wherein the gel formation is selected to be reversible,
    wherein the given temperature or temperature range is at or near normal body temperature for a human or animal patient, or at or near the optimum incubation temperature for tissue grown in vitro on the scaffold,
    wherein the fluid and scaffold allow a biological marker to infiltrate into the fluid.

2. A device according to claim 1, wherein each triblock copolymer has a molecular weight for the PLGA end blocks in the range 1,500-3,000 and a molecular weight for the central PEG block of 1,000 or 1,500.

3. A device according to claim 1, wherein substantially all of the fluid is a relatively low viscosity liquid at room temperature.

4. A device according to claim 1, wherein the fluid is or comprises:
    a 10-50 w/v % aqueous solution of one or more reversibly thermo-switchable gel materials.

5. A device according to claim 1, wherein the mean fibre diameter of the scaffold fibres is from about 1.9 to 2.8 microns.

6. A device according to claim 1, wherein the fluid penetrates entirely into the scaffold.

7. The sampling device of claim 1, wherein the biological marker is selected from the group consisting of: a microbial product, a microbial cell, a part of a microbial cell, and a substance or cell associated with a living human or animal body's response to a microbe, a wound or endocrine or metabolic condition.

8. The sampling device of claim 1, wherein each of the one or more thermo-switchable gel materials is a triblock copolymer which contains a poly(lactic acid-co-glycolic acid) (PLGA) random copolymer end blocks and a poly(ethylene glycol) (PEG) homopolymer central block.

\* \* \* \* \*